United States Patent
Cederna et al.

(10) Patent No.: US 12,070,565 B2
(45) Date of Patent: Aug. 27, 2024

(54) DEVICE AND METHOD FOR WOUND IRRIGATION AND DEBRIDEMENT

(71) Applicant: THE REGENTS OF THE UNIVERSITY OF MICHIGAN, Ann Arbor, MI (US)

(72) Inventors: Paul Stephen Cederna, Grass Lake, MI (US); Nishant Ganesh Kumar, Ann Arbor, MI (US); Jeffrey Stephen Plott, Algonac, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 98 days.

(21) Appl. No.: 17/428,557

(22) PCT Filed: Feb. 4, 2020

(86) PCT No.: PCT/US2020/016594
§ 371 (c)(1),
(2) Date: Aug. 4, 2021

(87) PCT Pub. No.: WO2020/163343
PCT Pub. Date: Aug. 13, 2020

(65) Prior Publication Data
US 2022/0126014 A1 Apr. 28, 2022

Related U.S. Application Data

(60) Provisional application No. 62/800,794, filed on Feb. 4, 2019.

(51) Int. Cl.
*A61M 3/02* (2006.01)
*A61M 1/00* (2006.01)

(52) U.S. Cl.
CPC ............ *A61M 3/0262* (2013.01); *A61M 1/77* (2021.05); *A61M 1/85* (2021.05); *A61M 2210/04* (2013.01)

(58) Field of Classification Search
CPC ............ A61M 1/77; A61M 1/85; A61M 1/87; A61M 3/0245; A61M 3/0262;
(Continued)

(56) References Cited

U.S. PATENT DOCUMENTS 3,324,855 A  6/1967 Heimlich
3,520,300 A  7/1970 Flower, Jr.
(Continued)

OTHER PUBLICATIONS

Agorastides, Ioannis et al., "A versatile protective shield for pulsatile jet irrigation," *Acta Orthopaedica Scandinavica*, 70(4), pp. 392-393; (Published online Jul. 8, 2009) DOI: 10.3109/17453679908997831.
(Continued)

*Primary Examiner* — Leslie A Lopez
*Assistant Examiner* — Timothy L Flynn
(74) *Attorney, Agent, or Firm* — Harness, Dickey & Pierce, P.L.C.

(57) ABSTRACT

A device for wound irrigation and debridement includes a body extending along a longitudinal axis. The body comprises an interior region and an opening such that that the interior region and the first opening are configured to transfer an irrigation fluid. The body comprises a compliant region having a first stiffness and a debridement region having a different second stiffness. The compliant region defines a distal surface. In a first configuration, the compliant region defines a first axial dimension, the distal surface engages a target body region, and the debridement region is axially offset from the distal surface and disengaged from the target body region. In a second configuration, the compliant region is compressed to define a second axial dimension less than the first axial dimension, thereby engaging the debridement region with the target body region, and the distal surface engages the target body region.

22 Claims, 19 Drawing Sheets

(58) Field of Classification Search
CPC .............. A61M 2210/04; A61B 17/54; A61B 2017/00761; A61B 2217/005; A61B 2217/007; A61B 2018/00577; A61B 2018/0047

See application file for complete search history.

(56) References Cited

U.S. PATENT DOCUMENTS

| | | |
|---|---|---|
| RE28,405 E | 5/1975 | Sollerud |
| 4,332,250 A | 6/1982 | Behney |
| 4,692,140 A | 9/1987 | Olson |
| 5,046,486 A | 9/1991 | Grulke et al. |
| 5,269,750 A | 12/1993 | Grulke et al. |
| 5,395,357 A | 3/1995 | Weigel |
| 5,441,174 A | 8/1995 | Sperry |
| 5,460,604 A | 10/1995 | Arnett et al. |
| 5,489,280 A | 2/1996 | Russell |
| 5,499,970 A | 3/1996 | Olson |
| 5,527,275 A | 6/1996 | Ginsberg |
| 5,624,419 A | 4/1997 | Ersek et al. |
| 5,735,833 A | 4/1998 | Olson |
| 5,848,998 A | 12/1998 | Marasco, Jr. |
| 6,099,494 A | 8/2000 | Henniges et al. |
| 6,156,004 A | 12/2000 | Tremaine et al. |
| 6,179,807 B1 | 1/2001 | Henniges et al. |
| 6,293,929 B1 | 9/2001 | Smith et al. |
| 6,299,620 B1 | 10/2001 | Shadduck et al. |
| 6,387,103 B2 | 5/2002 | Shadduck |
| 6,402,724 B1 | 6/2002 | Smith et al. |
| 6,485,452 B1 | 11/2002 | French et al. |
| 6,558,344 B2 | 5/2003 | McKinnon et al. |
| 6,562,013 B1 | 5/2003 | Marasco, Jr. |
| 6,629,983 B1 | 10/2003 | Ignon |
| 6,641,591 B1 | 11/2003 | Shadduck |
| D490,517 S | 5/2004 | Harmon |
| D490,518 S | 5/2004 | Harmon et al. |
| 6,830,556 B2 | 12/2004 | Harmon et al. |
| 6,902,557 B2 | 6/2005 | Mezzoli et al. |
| 7,143,763 B2 | 12/2006 | Abate |
| 7,662,125 B2 | 2/2010 | Rucinski |
| 7,678,092 B2 | 3/2010 | Matloub et al. |
| 7,771,402 B2 | 8/2010 | Marasco |
| 7,789,886 B2 | 9/2010 | Shadduck |
| 8,048,089 B2 | 11/2011 | Ignon et al. |
| 8,137,306 B2 | 3/2012 | Henniges et al. |
| 8,337,513 B2 | 12/2012 | Shadduck |
| 8,568,375 B2 | 10/2013 | Marasco |
| 8,657,796 B2 | 2/2014 | Marasco |
| 9,050,133 B1 | 6/2015 | Boone, III et al. |
| 9,107,985 B2 | 8/2015 | Hirsch |
| 9,308,024 B2 | 4/2016 | Whyte et al. |
| 9,655,432 B2 * | 5/2017 | Boone, III .............. A61B 17/54 |
| 9,775,646 B2 | 10/2017 | Shadduck |
| 10,105,481 B2 | 10/2018 | Henniges et al. |
| 10,154,855 B2 | 12/2018 | Hall et al. |
| 10,265,071 B2 | 4/2019 | Seegert |
| 2004/0092895 A1 | 5/2004 | Harmon |
| 2004/0116903 A1 | 6/2004 | Osman |
| 2004/0122447 A1 | 6/2004 | Harmon et al. |
| 2006/0008419 A1 | 1/2006 | Hissink et al. |
| 2006/0293630 A1 | 12/2006 | Manna et al. |
| 2008/0052850 A1 * | 3/2008 | McKay ................ A01K 13/002 132/119 |
| 2008/0065001 A1 | 3/2008 | DiNucci et al. |
| 2008/0287890 A1 | 11/2008 | Foster |
| 2008/0287891 A1 | 11/2008 | Foster |
| 2009/0131891 A1 | 5/2009 | Fons |
| 2009/0326489 A1 | 12/2009 | Kensy et al. |
| 2010/0030132 A1 | 2/2010 | Niezgoda et al. |
| 2014/0276626 A1 * | 9/2014 | Jenkins ............... A61M 3/0279 604/514 |
| 2015/0182078 A1 * | 7/2015 | Miller .................... A46B 13/04 15/104.93 |
| 2015/0258257 A1 | 9/2015 | Kidman et al. |
| 2016/0067401 A1 | 3/2016 | Henniges et al. |
| 2016/0199566 A1 | 7/2016 | Schug et al. |
| 2017/0049641 A1 | 2/2017 | Moser et al. |
| 2019/0184146 A1 | 6/2019 | Moore |
| 2019/0224402 A1 | 7/2019 | Henry et al. |
| 2020/0405945 A1 * | 12/2020 | Schug ................. A61M 3/0283 |

OTHER PUBLICATIONS

Angobaldo, J. et al., "Prevention of Projectile and Aerosol Contamination During Pulsatile Lavage Irrigation Using a Wound Irrigation Bag," *Wounds Research*, 20, 7 (Jun. 2008); <URL: https://www.woundsresearch.com/article/8881>.

Koniaris, Leonidas G. et al., "Bag lavage: a closed method for pulse lavage irrigation," *Journal of the American College of Surgeons: Surgeon at Work*, 191,4 (Oct. 2000), pp. 466-468; DOI: 10.1016/S1072-7515(00)00693-1.

Maragakis, Lisa L. et al., "An Outbreak of Multidrug-Resistant Acinetobacter baumannii Associated With Pulsatile Lavage Wound Treatment," *JAMA*. (2004) 292(24), pp. 3006-3011; DOI: 10.1001/jama.292.24.3006.

Mote, Gregory A. et al., "Efficacy of Power-pulsed Lavage in Lower Extremity Wound Infections: A Prospective Observational Study," *The Journal of Foot and Ankle Surgery*, 49, 2 (2010), pp. 135-142; DOI: 10.1053/j.jfas.2009.10.004.

Sen, Chandan K. et al., "Human skin wounds: a major and snowballing threat to public health and the economy," Wound repair and regeneration : official publication of the Wound Healing Society [and] the European Tissue Repair Society, vol. 17, 6 (2009), pp. 763-771. DOI:10.1111/j.1524-475X.2009.00543.x.

"Guideline for Isolation Precautions: Preventing Transmission of Infectious Agents in Heathcare Settings," *Centers for Disease Control and Prevention* (2007), [retrieved from the Internet] [retrieved on Jan. 7, 2020] <URL: https://www.cdc.gov/infectioncontrol/guidelines/isolation/prevention.html>, 29 pages.

Pulsavac® Plus Wound Debridement. Datasheet [online]. Zimmer Biomet ©, 2017 [retrieved on Jan. 7, 2020]. Retrieved from the Internet: <URL: https://www.zimmerbiomet.com/medical-professionals/surgical-and-operating-room-solutions/product/pulsavac-plus-products.html>.

PulseCare™ Closed Pulse Irrigation™ Product Applications. Datasheet. PulseCase Medical, LLC, 5 pages.

"Reverse, Fight, and Defend Against the Sources of SSI," *Prescient Surgical*, [retrieved on Jan. 3, 2019]. Retrieved from the Internet: <URL: https://www.prescientsurgical.com/cleancision>.

International Search Report and Written Opinion of the International Searching Authority issued in PCT/US2020/016594, mailed on Apr. 27, 2020; ISA/US.

\* cited by examiner

DEVICE AND METHOD FOR WOUND IRRIGATION AND DEBRIDEMENT

CROSS-REFERENCE TO RELATED APPLICATIONS

This application is the U.S. National Phase Application under 35 U.S.C. 371 of International Application No. PCT/US2020/016594 filed on Feb. 4, 2020, which claims the benefit of U.S. Provisional Application No. 62/800,794, filed on Feb. 4, 2019. The entire disclosures of the above applications are incorporated herein by reference.

FIELD

The present disclosure relates to irrigation and debridement of wounds, and more particularly to an assembly for irrigation of wounds, containment of wound debris and irrigation fluid, and mechanical debridement of wounds.

BACKGROUND

This section provides background information related to the present disclosure which is not necessarily prior art.

Wounds are often managed using local wound care with dressing changes, irrigation and debridement. Irrigation or hydrotherapy (with a saline or antibiotic solution) can clean the wound by flushing out foreign matter, such as dirt and bacteria. Irrigation can also debride the wound by washing away wound debris, such as dead or non-viable tissue. In addition to hydrotherapy, the wound may also be treated via mechanical debridement (e.g., scrubbing or surgical intervention). Advantageously, irrigation and debridement of wounds may be performed concurrently.

SUMMARY

This section provides a general summary of the disclosure, and is not a comprehensive disclosure of its full scope or all of its features.

Advantageously, the present disclosure in certain variations provides a device for wound irrigation and debridement comprising a body. The body extends along a longitudinal axis. The body comprises an interior region and a first opening such that that the interior region and the first opening are configured to transfer an irrigation fluid. The body comprises a compliant region and a debridement region. The compliant region has a first stiffness. The compliant region includes a distal surface. The debridement region has a second stiffness different than the first stiffness. In a first configuration, the compliant region defines a first axial dimension along the longitudinal axis, the distal surface of the compliant region engages a target region, and the debridement region is axially offset from the distal surface and disengaged from the target region. In a second configuration, the compliant region is compressed along the longitudinal axis to define a second axial dimension less than the first axial dimension, thereby engaging the debridement region with the target region, and the distal surface of the compliant region engages the target region.

In one aspect, the second stiffness is greater than the first stiffness.

In one aspect, the compliant region is porous and defines a plurality of pores.

In one aspect, the compliant region comprises an open cell foam comprising the plurality of pores.

In one aspect, the pores of the plurality of pores have an average diameter of greater than or equal to about 0.2 mm to less than or equal to about 1 mm.

In one aspect, the compliant region has a porosity of greater than or equal to about 80%.

In one aspect, the compliant region comprises a polymer selected form the group consisting of: polyurethane, polyethylene, cellulose, silicone, thermoplastic elastomer, thermoplastic polyurethane, polyvinyl chloride (PVC), and combinations thereof.

In one aspect, the compliant region comprises a first material and the debridement region comprises a second material. The first and second materials are distinct from one another.

In one aspect, the compliant region further comprises an inner surface at least partially defining the interior region. The debridement region is coupled to the inner surface and extends inward toward the longitudinal axis from the inner surface. The debridement region defines a central opening substantially coaxial with the first opening.

In one aspect, the compliant region defines a cavity extending from the distal surface. The cavity is disposed outward of the interior region with respect to the longitudinal axis. The debridement region is disposed within the cavity.

In one aspect, at least a portion of the body defines a substantially cylindrical shape.

In one aspect, the debridement region defines a substantially annular shape and has a second opening substantially coaxial with the first opening.

In one aspect, the debridement region comprises a plurality of discrete debridement regions distributed about the longitudinal axis.

In one aspect, the debridement region comprises at least one of: a plurality of bristles, a plurality of protrusions, a plurality of non-woven fibers, a plurality of woven fibers, a mesh, an open cell foam, a closed cell foam, a plurality of particles, or a surface coating.

In one aspect, the device further comprises a frame embedded in the compliant region. The frame is disposed outward of the interior region with respect to the longitudinal axis. The frame comprises a ductile material. The frame is configured to be deformed to modify a shape of the compliant region.

In one aspect, the device further comprises a fastener engaging the body.

In one aspect, the fastener extends around an outer surface of the body. The fastener is configured to compress the body to reduce a dimension of the body.

In one aspect, the device further comprises an impermeable layer disposed on at least a portion of an outer surface of the body.

Advantageously, the present disclosure in certain variations provides a device for wound irrigation and debridement comprising a body. The body extends along a longitudinal axis. The body comprises an interior region and an opening such that that the interior region and the opening are configured to transfer an irrigation fluid. The body comprises a compliant region and a debridement region. The compliant region has a first density and defines a distal surface. The debridement region has a second density greater than the first density. In a first configuration, the compliant region defines a first axial dimension along the longitudinal axis, the distal surface of the compliant region engages a target region, and the debridement region is axially offset from the distal surface and disengaged from the target region. In a second configuration, the compliant region is compressed along the longitudinal axis to define a second axial dimension less than the first axial dimension, thereby engaging the debridement region with the target region, and the distal surface of the compliant region engages the target region.

Advantageously, the present disclosure in certain variations provides a device for wound irrigation and debridement comprising a body. The body extends along a longitudinal axis. The body comprises an interior region and an opening such that that the interior region and the opening are configured to transfer an irrigation fluid. The body comprises a compliant region and a debridement region. The compliant region comprises a first material and defines a distal surface. The debridement region is coupled to a surface of the compliant region. The debridement region comprises a second material different from the first material. In a first configuration, the compliant region defines a first axial dimension along the longitudinal axis, the distal surface of the compliant region engages a target region, and the debridement region is axially offset from the distal surface and disengaged from the target region. In a second configuration, the compliant region is compressed along the longitudinal axis to define a second axial dimension less than the first axial dimension, thereby engaging the debridement region with the target region, and the distal surface of the compliant region engages the target region.

Advantageously, the present disclosure in certain variations provides a device and nozzle assembly for wound irrigation. The assembly comprises a nozzle and a device. The nozzle is configured to receive irrigation fluid and deliver the irrigation fluid to a target region. The device is coupled to the nozzle. The device comprises a body extending along a longitudinal axis. The body includes an interior region and an opening, such that the interior region and the opening are configured to transfer the irrigation fluid. The device comprises a compliant region defining a first stiffness. The compliant region defines a distal surface. At least one of the nozzle and the device comprises a debridement region defining a second stiffness different than the first stiffness. In a first configuration, the compliant region defines a first axial dimension along the longitudinal axis, the distal surface of the compliant region engages the target region, and the debridement region is axially offset from the distal surface and disengaged from the target region. In a second configuration, the compliant region is compressed along the longitudinal axis to define a second axial dimension less than the first axial dimension, thereby engaging the debridement region with the target region, and the distal surface of the compliant region engages the target region.

In one aspect the nozzle comprises the debridement region. The debridement region is disposed on a distal end of the nozzle.

In one aspect, the body defines the debridement region. The body is configured to engage the target region in the first configuration, the second configuration, and a third configuration. In the third configuration, the compliant region is compressed along the longitudinal axis to define a third axial dimension less than the second axial dimension, thereby engaging the nozzle with the debridement region and the debridement region with the target region, and the distal surface of the compliant region engages the target region.

In one aspect, the interior region of the body is configured to receive a vacuum port. The compliant region is configured to conform to the target region to create a fluid seal and pull negative pressure.

In one aspect, the device further comprises a tip. The tip defines a passage. The tip is in fluid communication with the nozzle. The tip is disposed at least partially within the interior region of the body.

In one aspect, at least a portion of the debridement region circumferentially surrounds at least a portion of the tip.

In one aspect, a portion of the debridement region is disposed within the passage.

Advantageously, the present disclosure in certain variations provides a method of irrigating and debriding a target region. The method comprises engaging a distal surface of an assembly with the target region. The assembly includes a nozzle and a device coupled to the nozzle. The device comprises a body extending along a longitudinal axis. The body includes an interior region. The distal surface comprises an opening. The body comprises a compliant region having a first stiffness and defining the distal surface and a debridement region having a second stiffness different than the first stiffness. The debridement region being disengaged from the target region. The method further includes discharging an irrigation fluid from the nozzle. The irrigation fluid is transferred through the interior region and the opening to contact the target region. The method further includes containing at least a portion of the irrigation fluid within one or both of the interior region and the compliant region. The method further includes compressing the device along the longitudinal axis such that the debridement region engages the target region.

In one aspect, the target region is a wound bed.

Advantageously, the present disclosure in certain variations provides an irrigation and debridement assembly comprising a nozzle, a suction port, a tip, and a device. The nozzle is configured to receive irrigation fluid and deliver the irrigation fluid to a target region. The suction port is configured to remove irrigation fluid from the target region. The tip is coupled to the suction port and the nozzle. The tip defines a passage in fluid communication with the suction port and the nozzle. The device is coupled to the tip. The device is configured to transfer irrigation fluid between the passage and the target region. The device comprises a compliant region and a debridement region. The compliant region includes a distal surface. The debridement region is coupled to the compliant region. The debridement region includes a debridement surface. In a first configuration, at least a portion of the debridement surface is offset from the distal surface by a distance. In a second configuration, the debridement surface and the distal surface cooperate to define a contact surface. The contact surface is configured to engage at least a portion of the target region. The device is movable between the first configuration and the second configuration by translating the at least a portion of the debridement surface with respect to the distal surface.

In one aspect, at least a portion of the debridement region circumferentially surrounds at least a portion of a periphery of the tip.

In one aspect, in a wrapped position, a surface of the compliant region is substantially cylindrical. In a relaxed position, the surface is substantially planar.

In one aspect, at least a portion of the debridement region is disposed in the passage of the tip.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 3A:
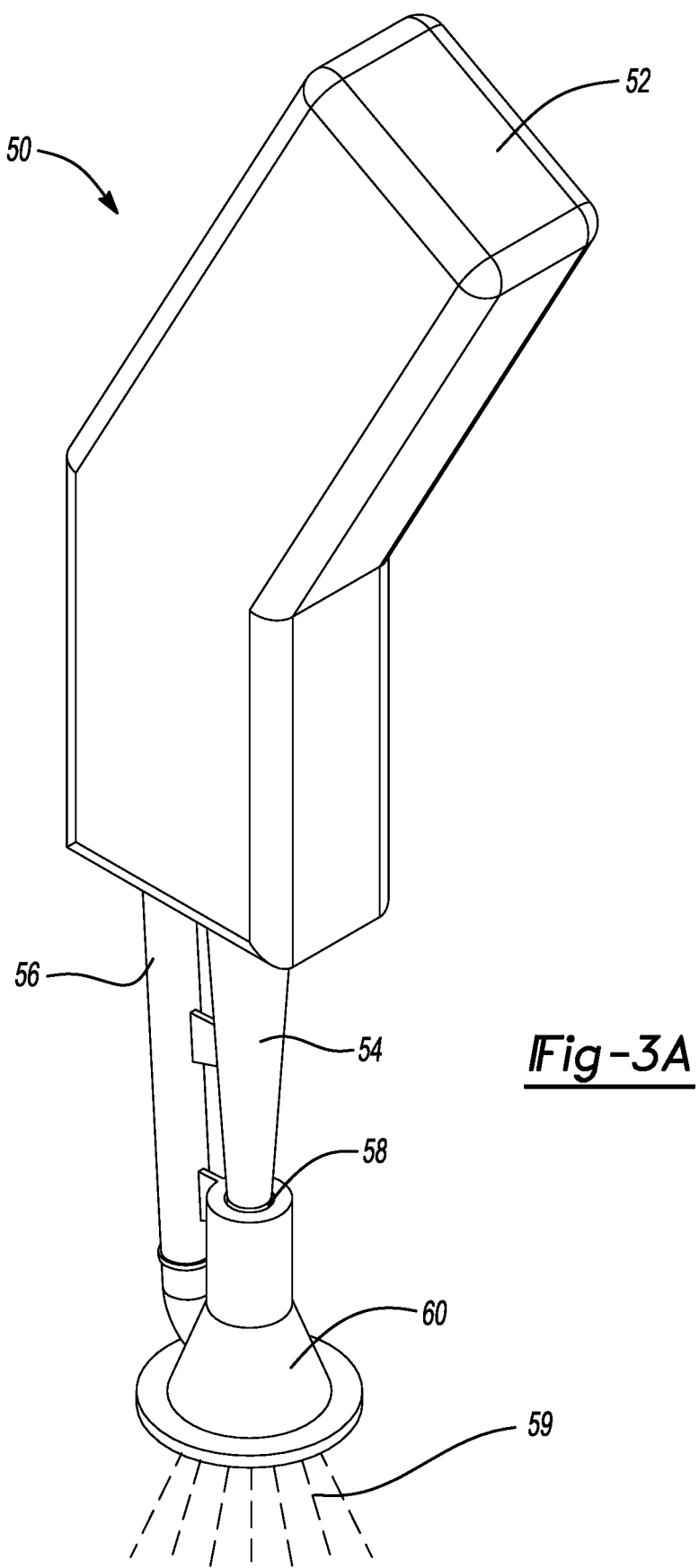
Figure 3B:
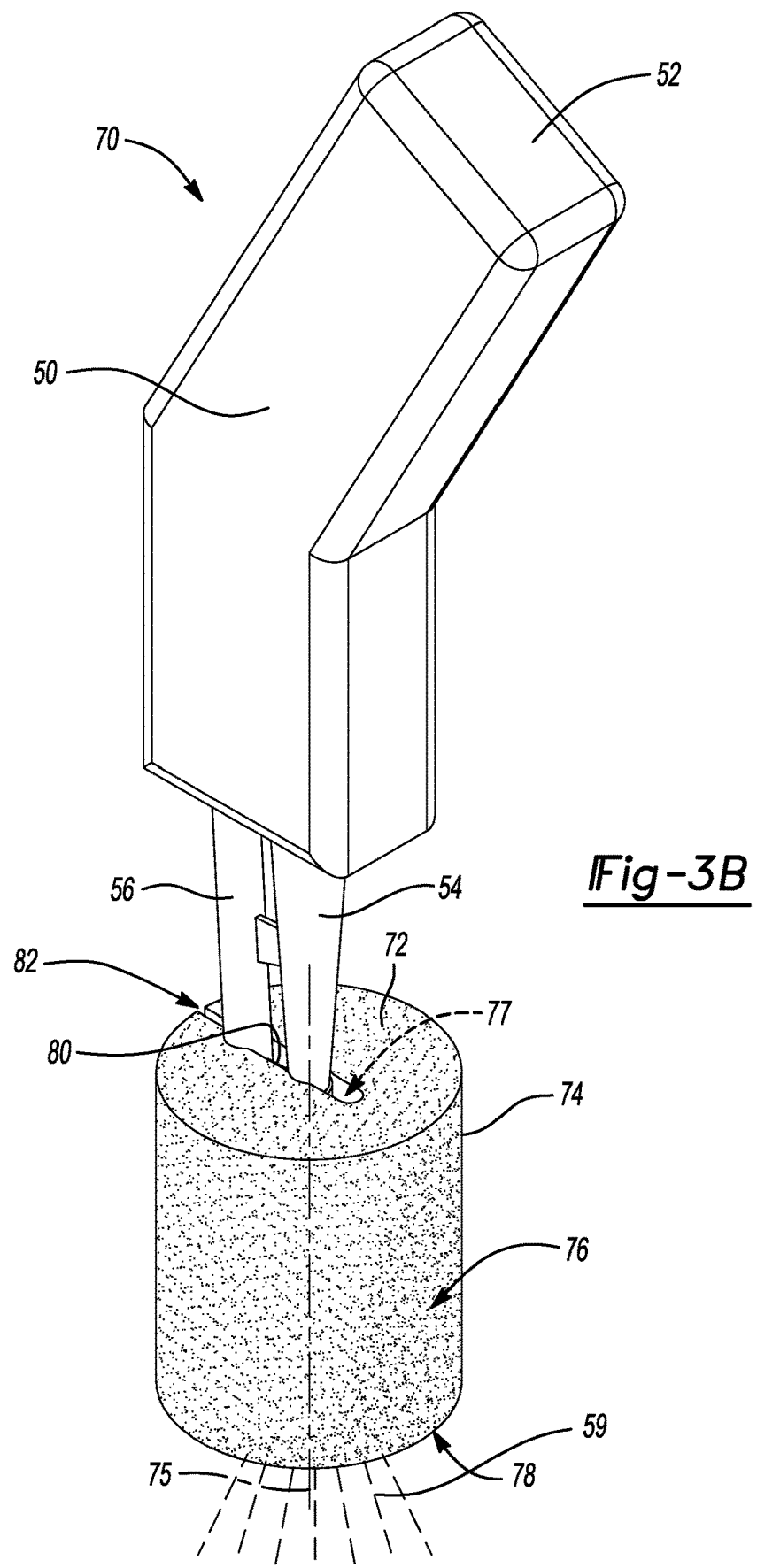
Figure 4A:
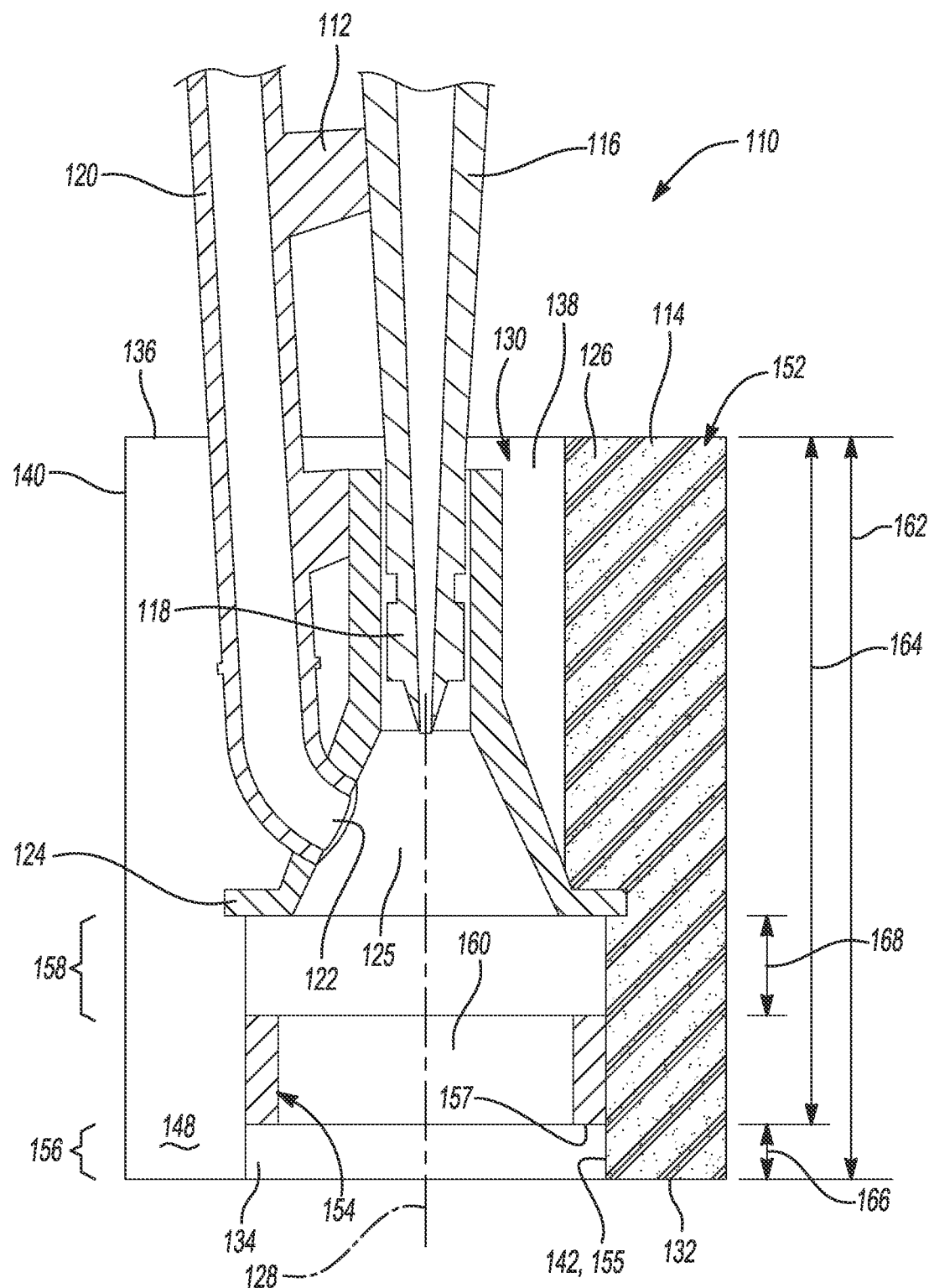
Figure 4B:
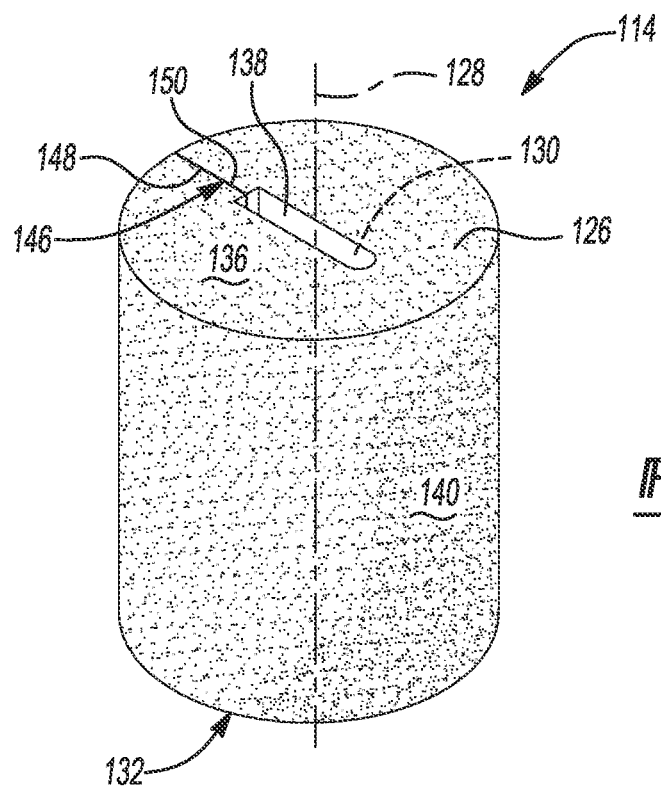
Figure 4C:
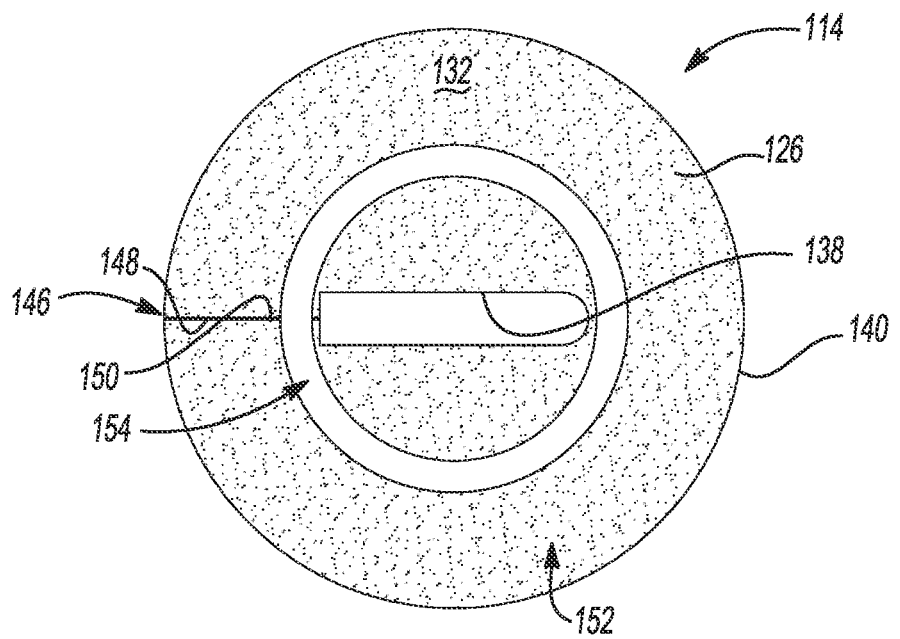
Figure 5:
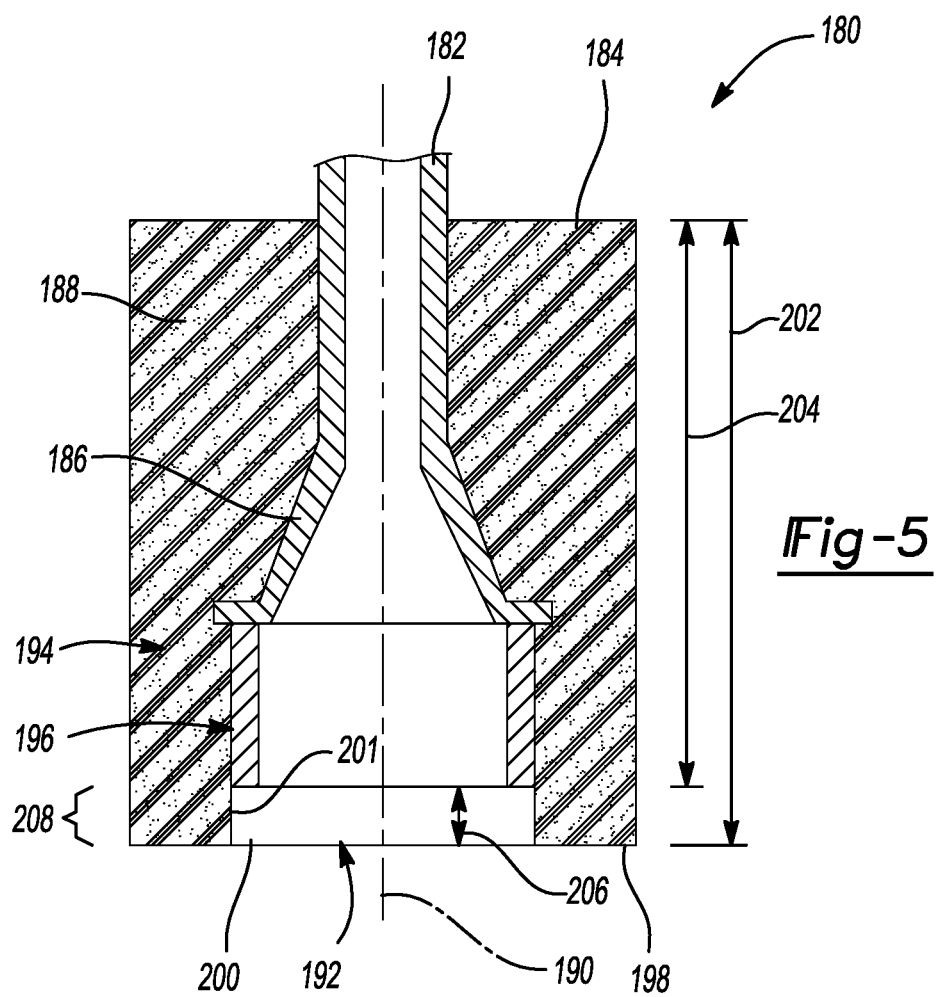
Figure 6A:
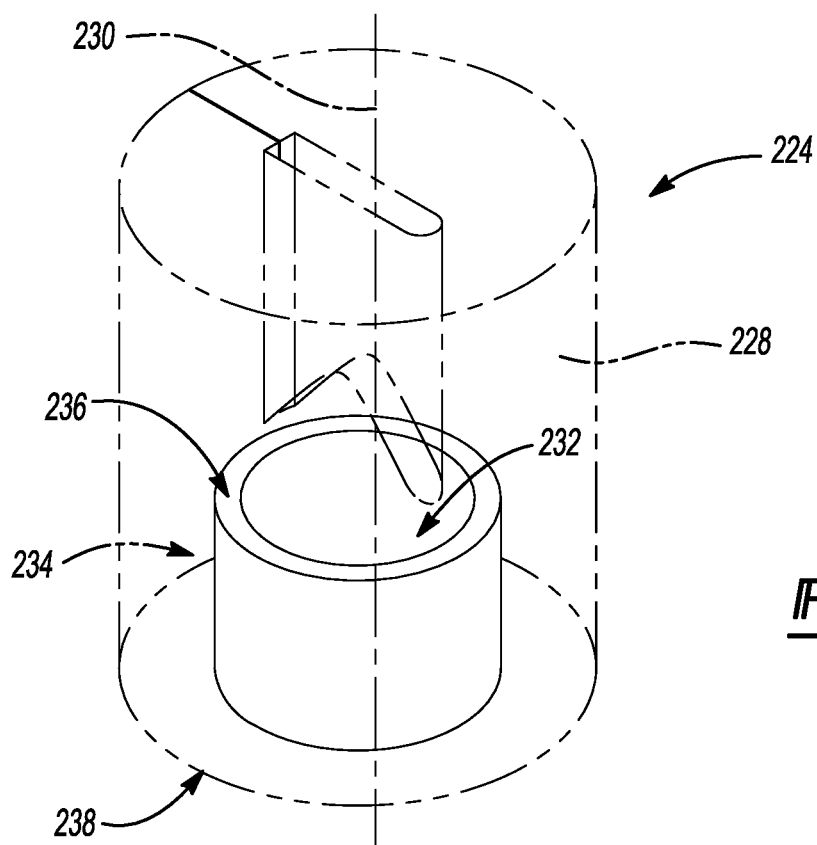
Figure 6B:
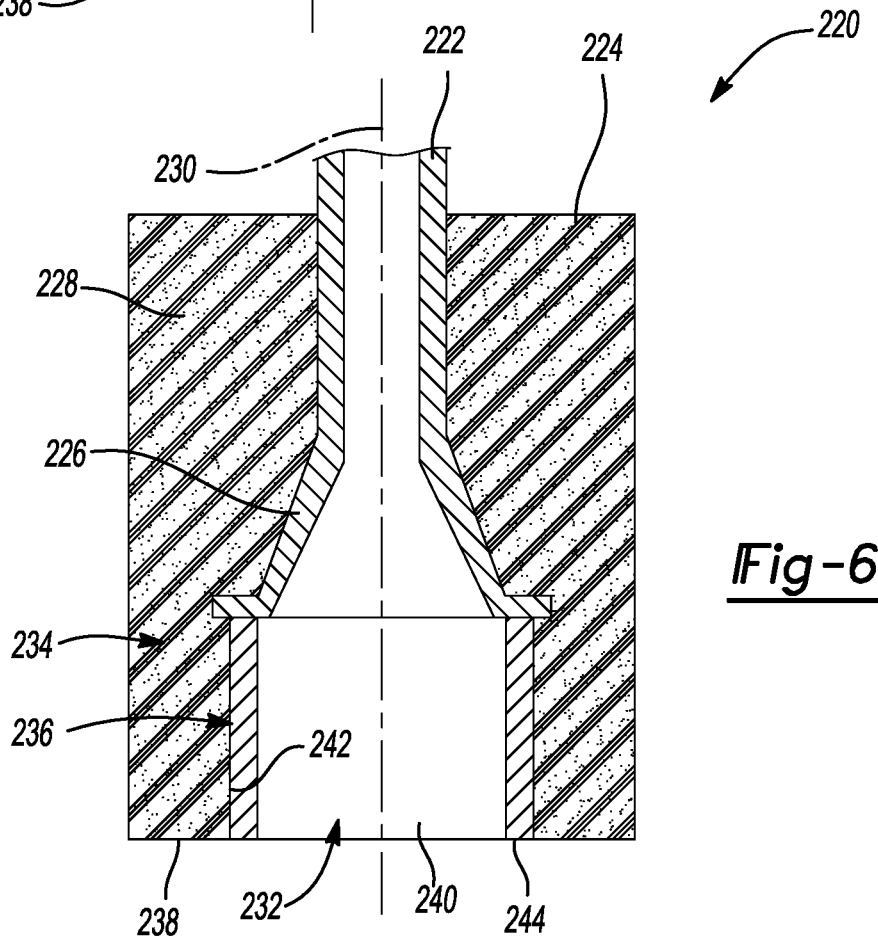
Figure 7A:
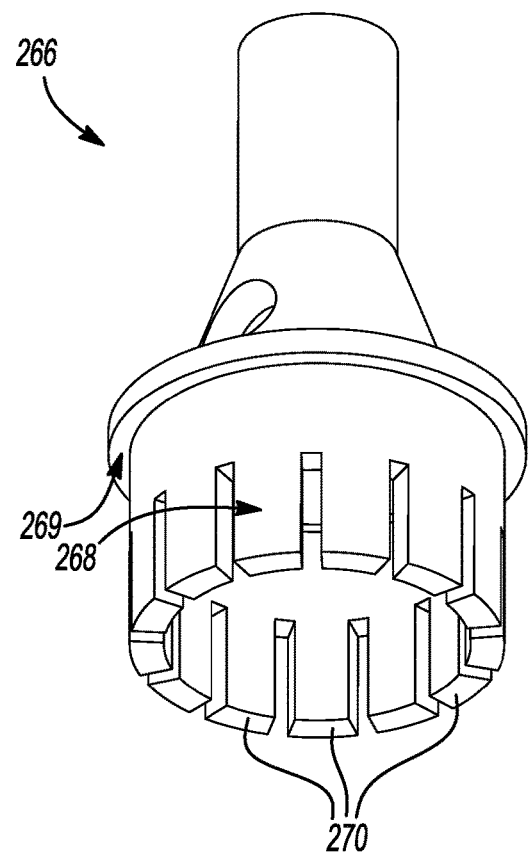
Figure 7B:
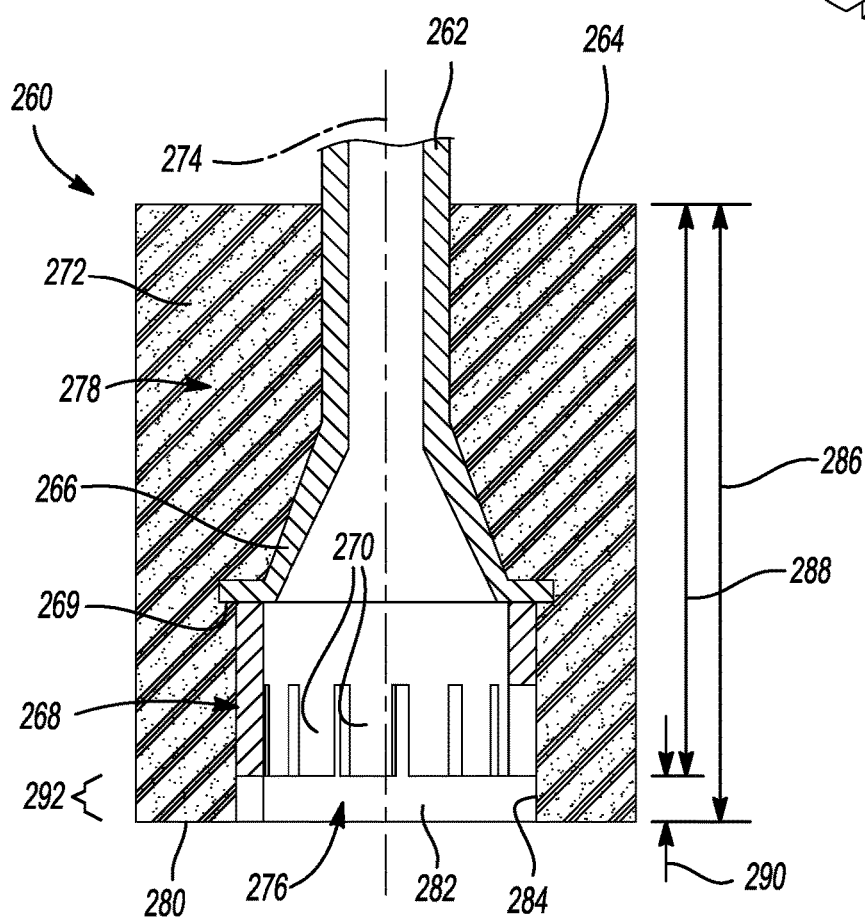
Figure 8A:
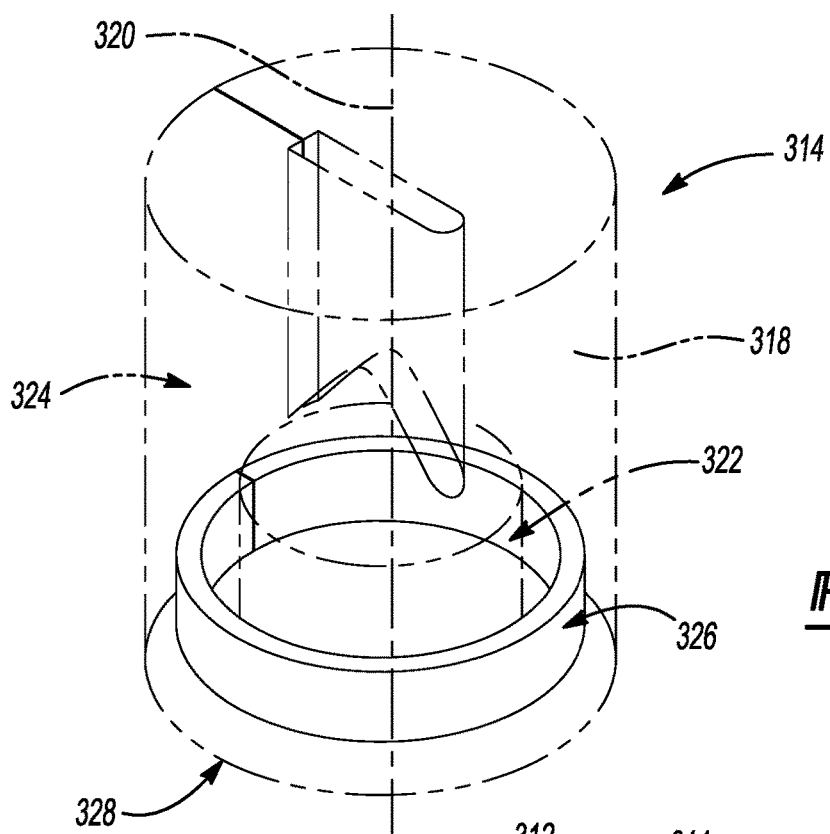
Figure 8B:
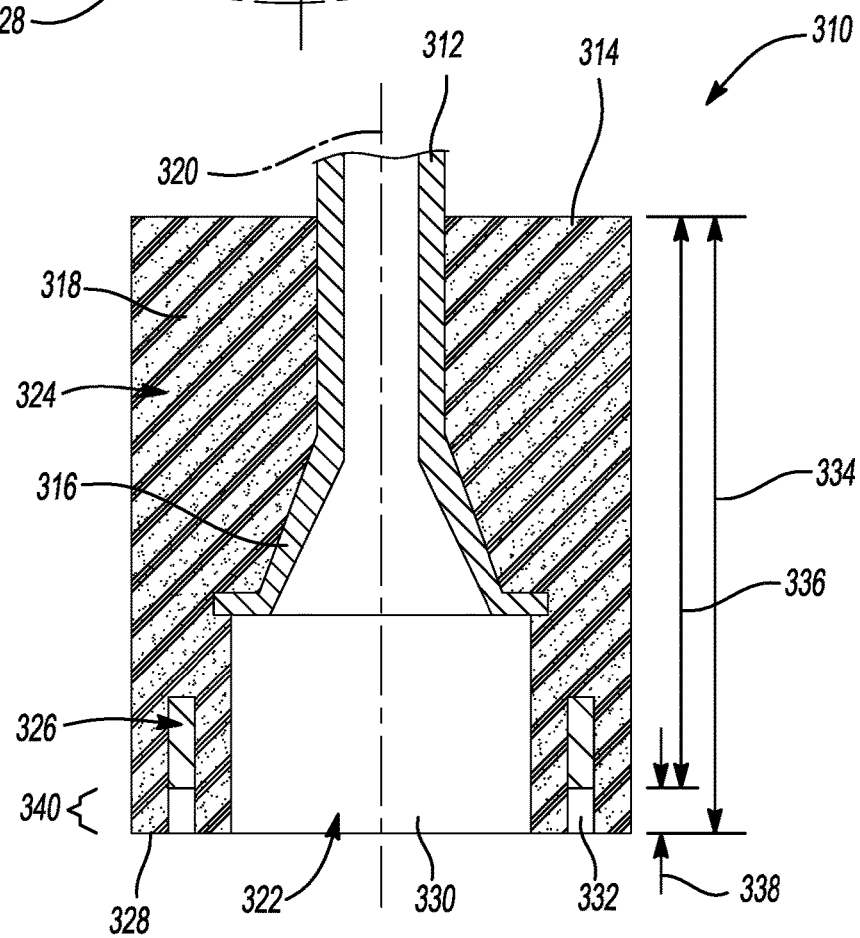
Figure 9A:
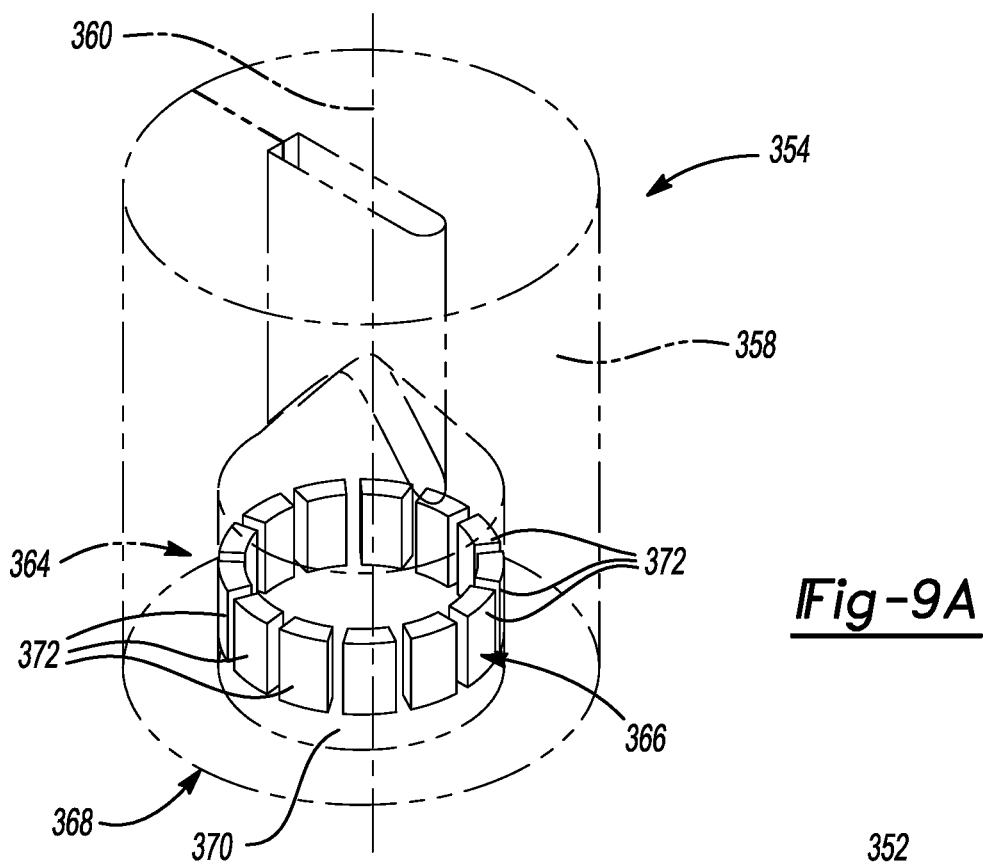
Figure 9B:
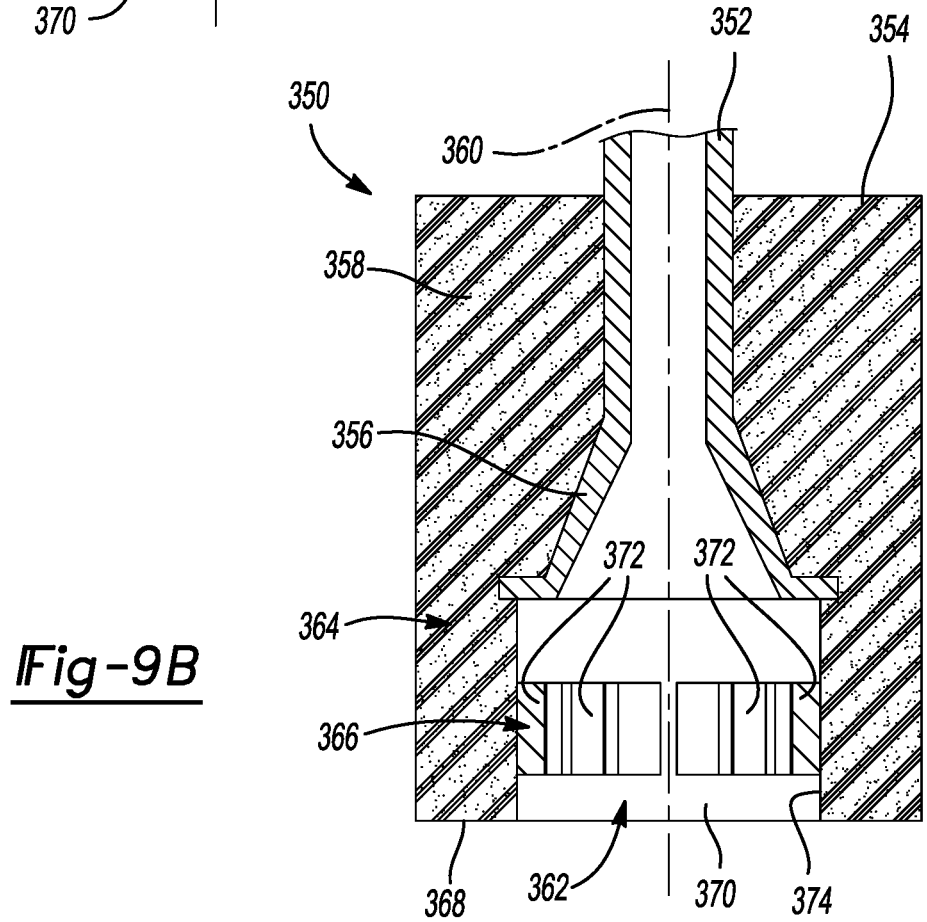
Figure 10:
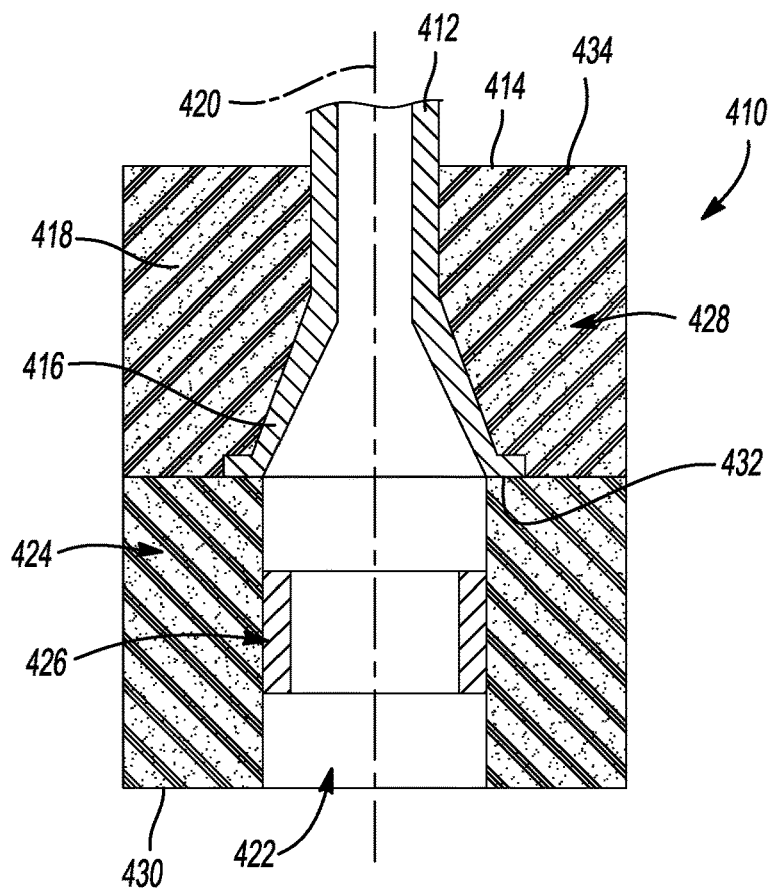
Figure 11:
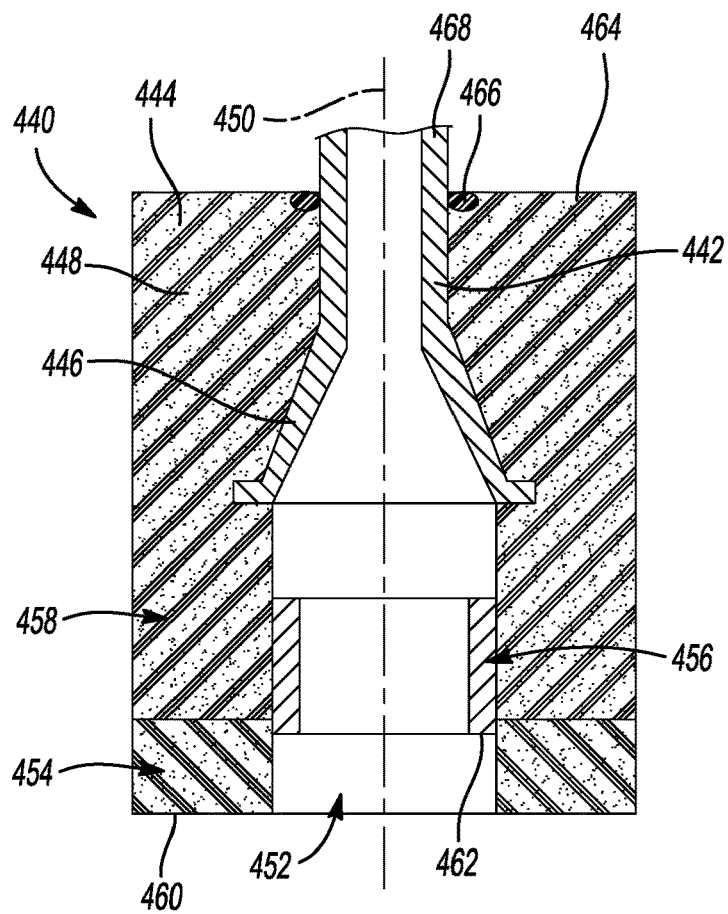
Figure 12:
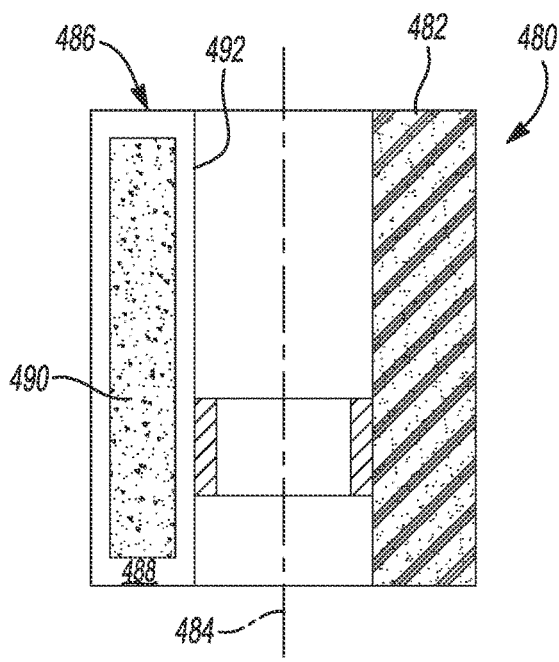
Figure 13:
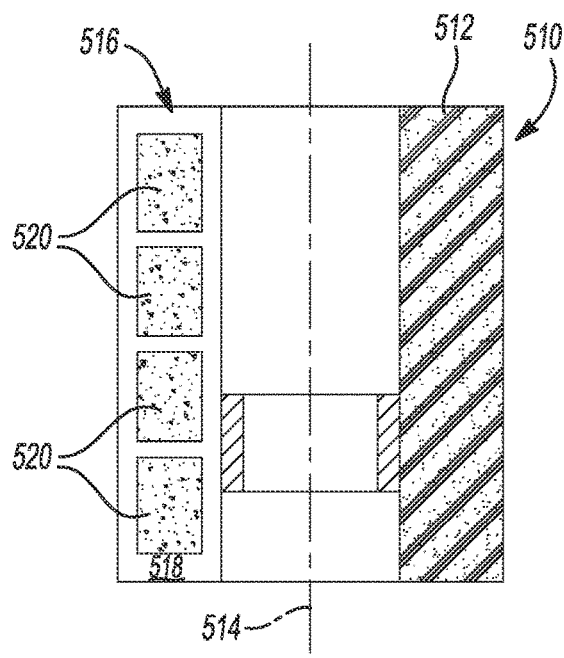
Figure 14:
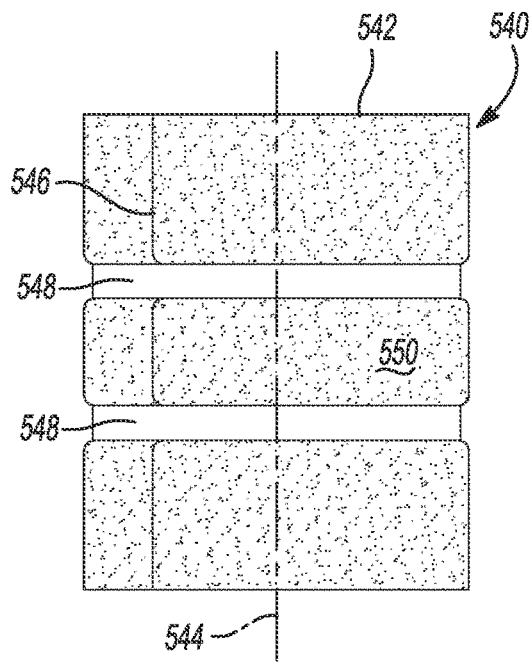
Figure 15:
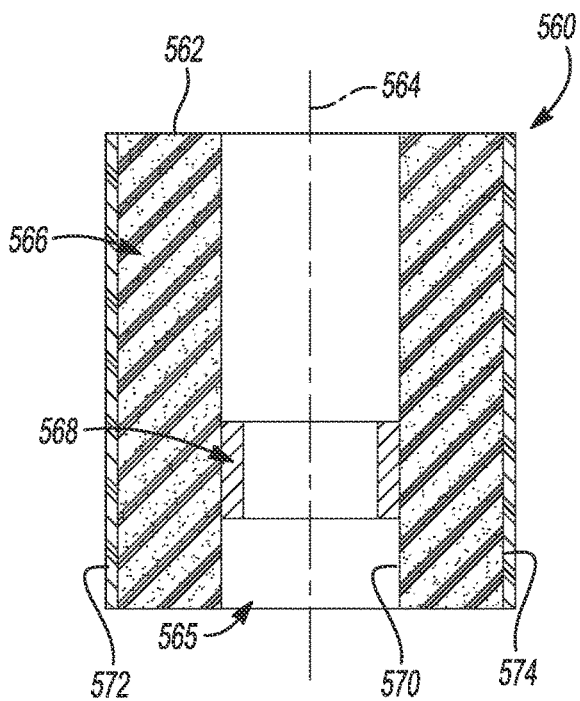
Figure 16A:
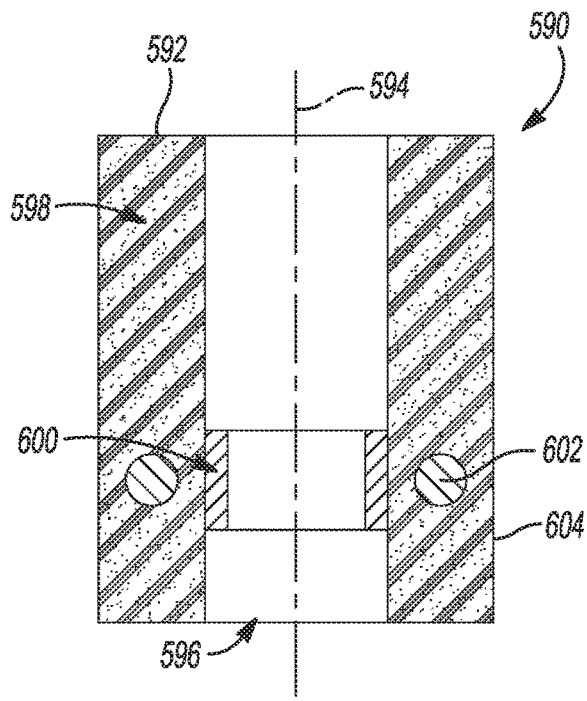
Figure 16B:
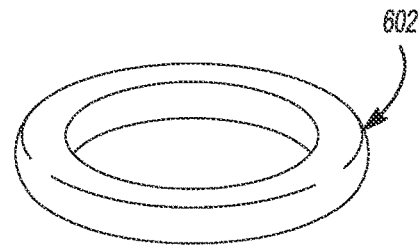
Figure 16C:
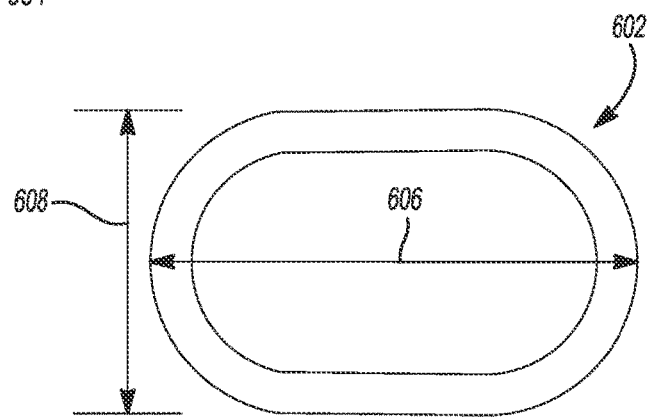
Figure 16D:
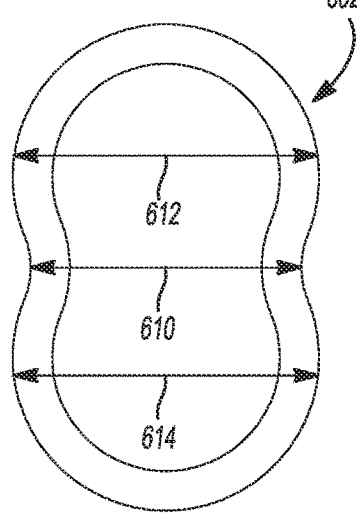
Figure 16E:
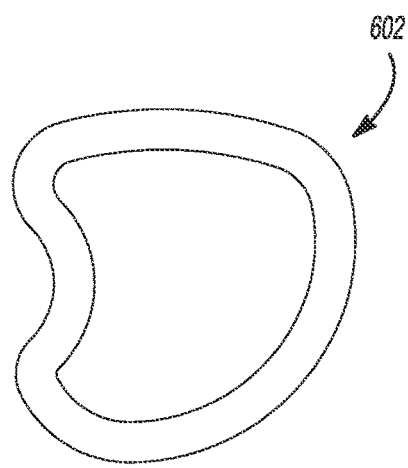
Figure 17:
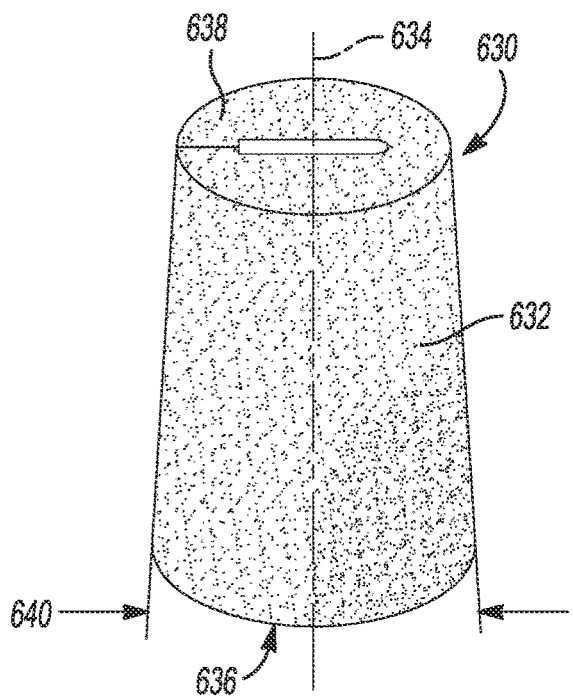
Figure 18:
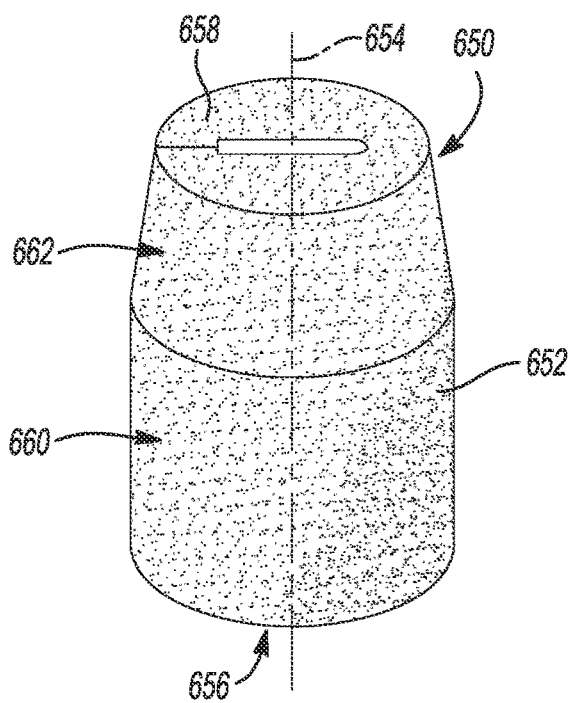
Figure 19:
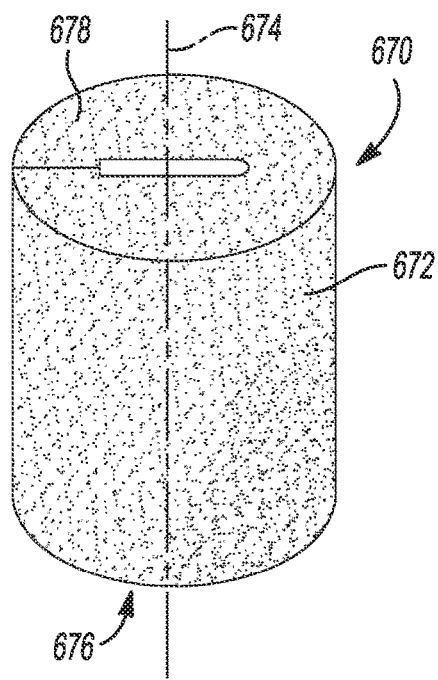
Figure 20:
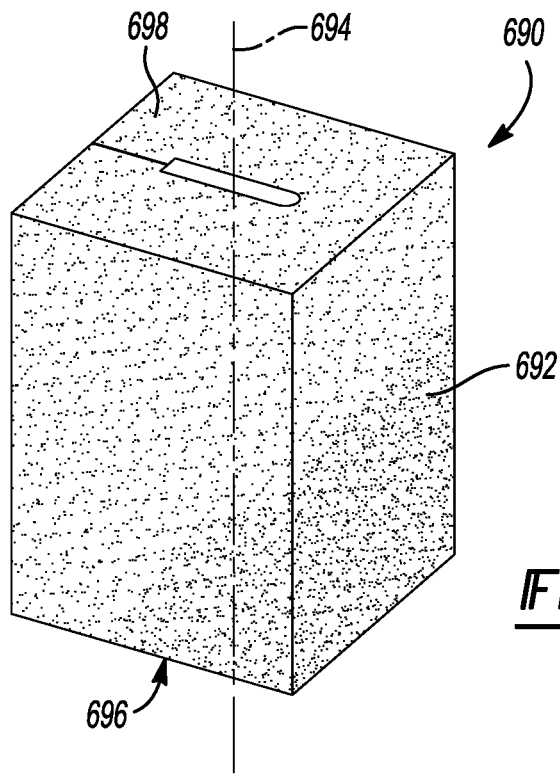
Figure 21:
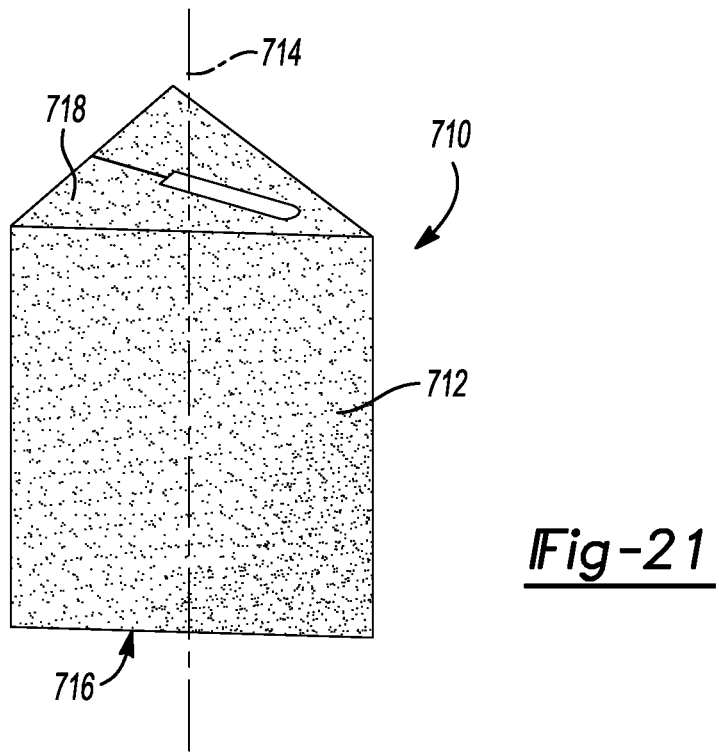
Figure 22A:
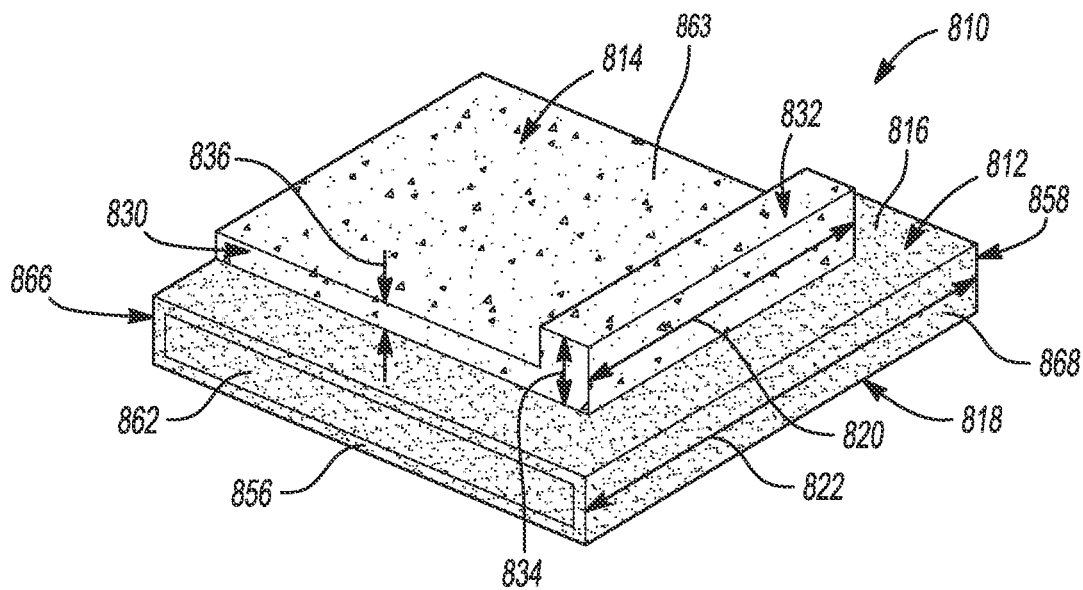
Figure 22B:
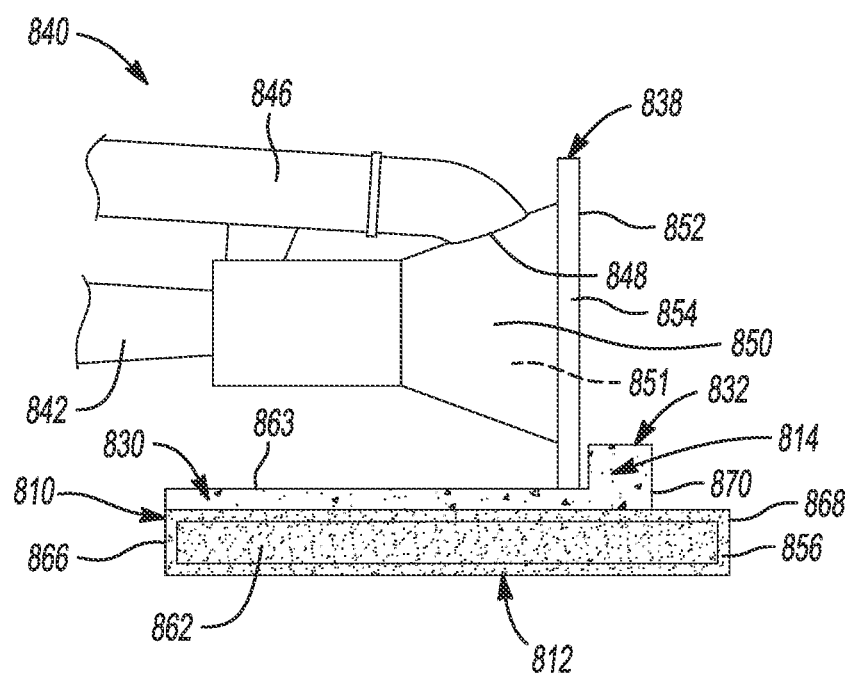
Figure 22C:
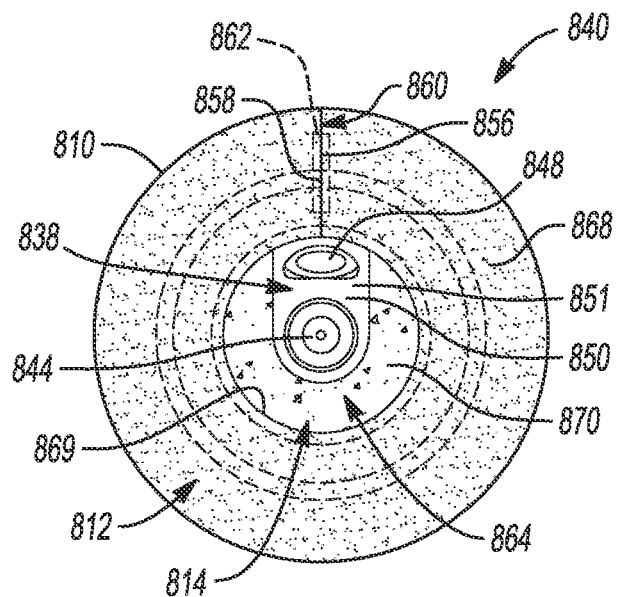
Figure 22D:
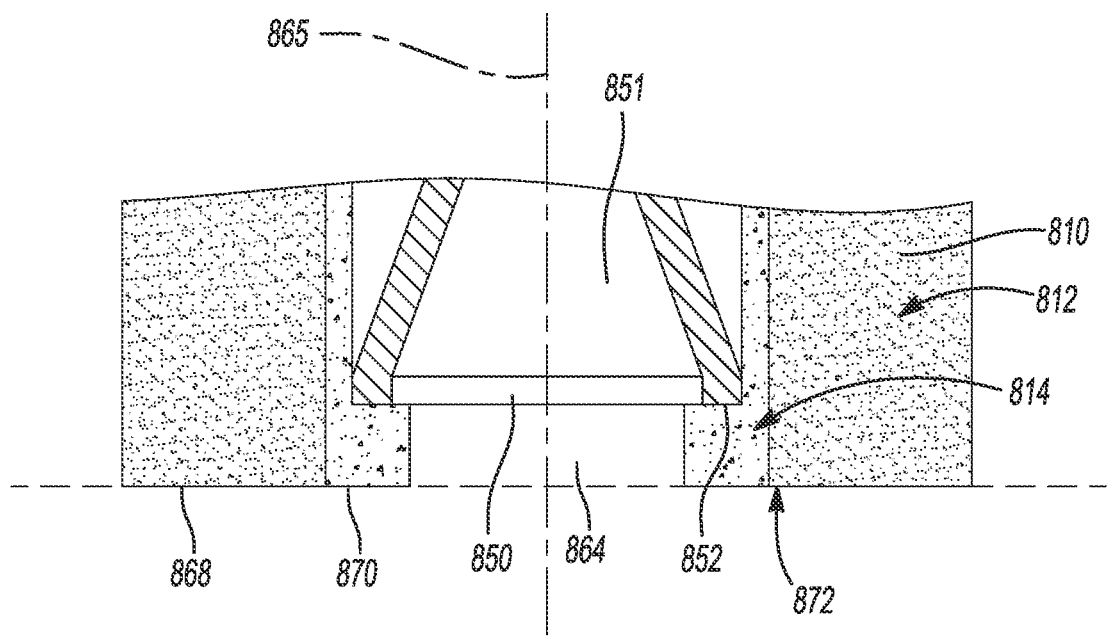
Figure 23A:
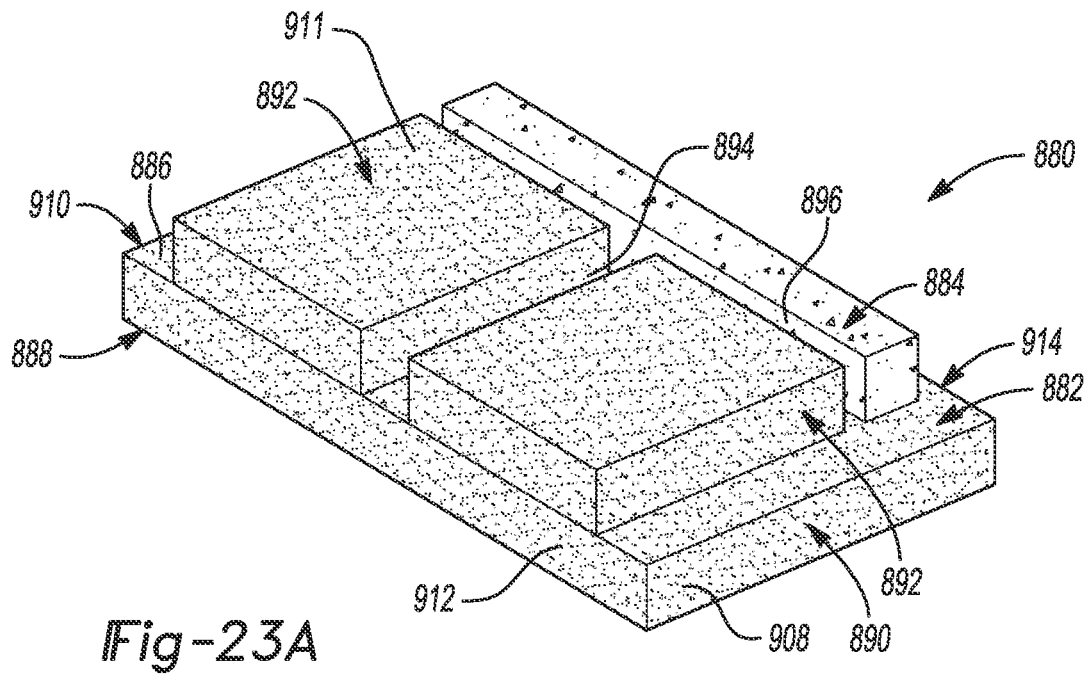
Figure 23B:
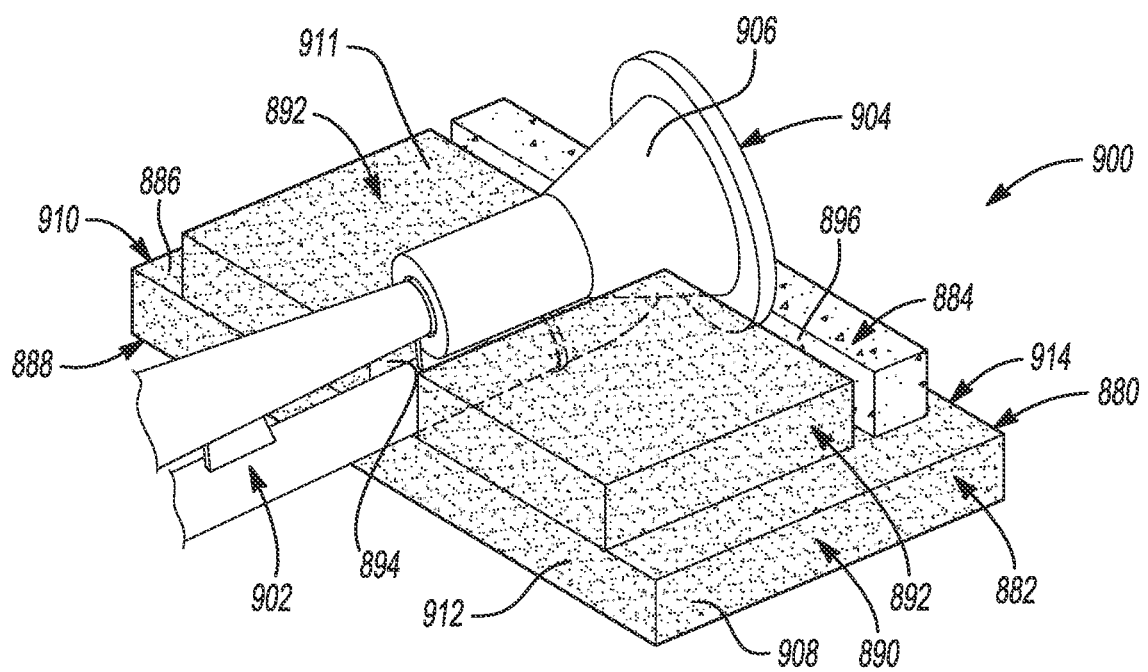
Figure 24A:
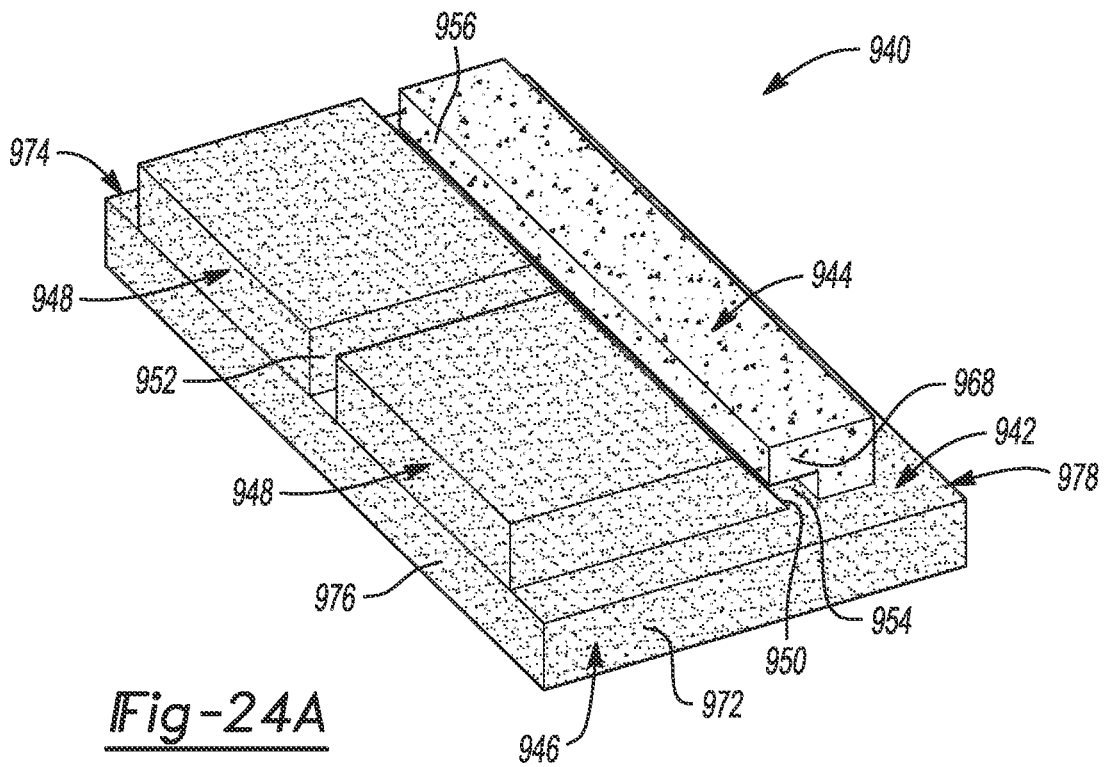
Figure 24B:
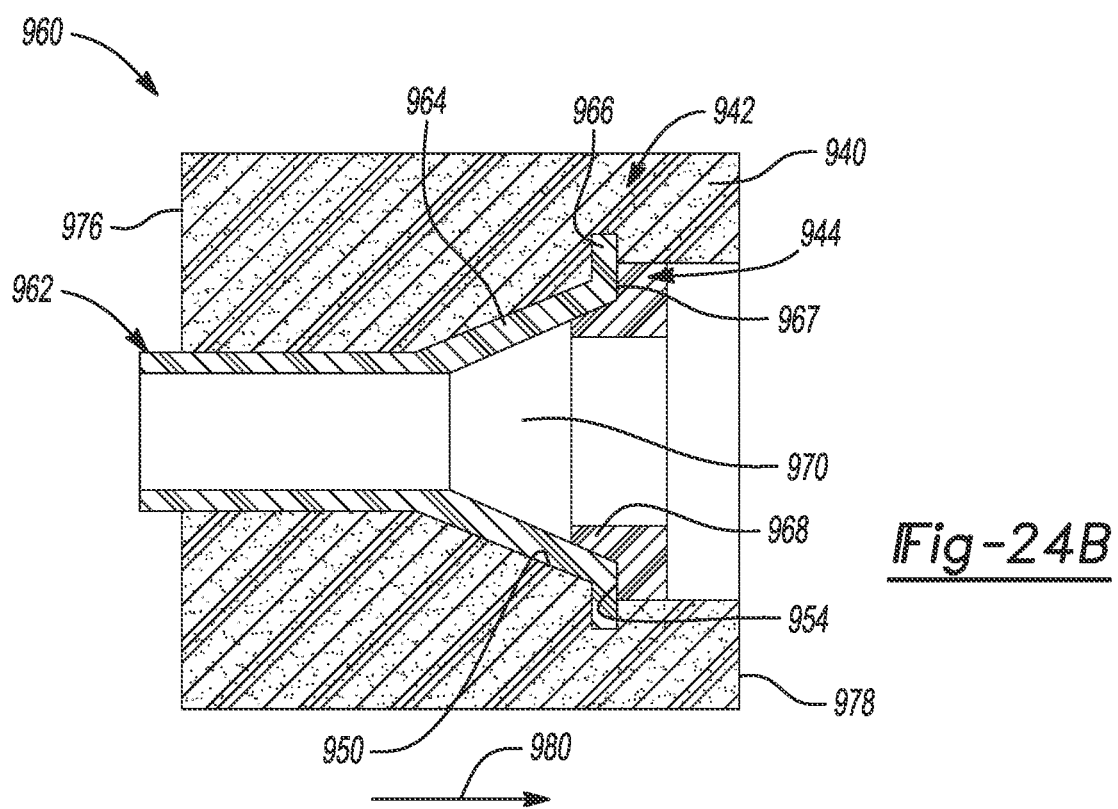

FIGS. 3A-3B relate to an irrigation and debridement assembly including a pulse lavage system according to various aspects of the present disclosure, FIG. 3A is a perspective view of the pulse lavage system, and FIG. 3B is a perspective view of the assembly;

FIGS. 4A-4C relate to an irrigation and debridement assembly according to various aspects of the present disclosure, FIG. 4A is a partial cross-sectional view of the assembly, FIG. 4B is a perspective view of a containment and debridement device of the assembly, and FIG. 4C is a bottom view of the device;

FIG. 5 is a partial cross-sectional view of another irrigation and debridement assembly according to various aspects of the present disclosure;

FIGS. 6A-6B relate to yet another irrigation and debridement assembly according to various aspects of the present disclosure, FIG. 6A is a perspective view of a containment and debridement device of the assembly, and FIG. 6B is a partial cross-sectional view of the assembly;

FIGS. 7A-7B relate to yet another irrigation and debridement assembly according to various aspects of the present disclosure, FIG. 7A is a perspective view of a nozzle of the assembly, and FIG. 7B is a partial cross-sectional view of the assembly;

FIGS. 8A-8B relate to yet another irrigation and debridement assembly according to various aspects of the present disclosure, FIG. 8A is a perspective view of a containment and debridement device of the assembly, and FIG. 8B is a partial cross-sectional view of the assembly;

FIGS. 9A-9B relate to yet another irrigation and debridement assembly according to various aspects of the present disclosure, FIG. 9A is a perspective view of a containment and debridement device of the assembly, and FIG. 9B is a partial cross-sectional view of the assembly;

FIG. 10 is a partial cross-sectional view of yet another irrigation and debridement assembly according to various aspects of the present disclosure;

FIG. 11 is a partial cross-sectional view of yet another irrigation and debridement assembly according to various aspects of the present disclosure;

FIG. 12 is a cross-sectional view of a containment and debridement device according to various aspects of the present disclosure;

FIG. 13 is a cross-sectional view of another containment and debridement device according to various aspects of the present disclosure;

FIG. 14 is a side view of yet another containment and debridement device according to various aspects of the present disclosure;

FIG. 15 is a cross-sectional view of a yet another containment and debridement device according to various aspects of the present disclosure;

FIGS. 16A-16E relate to yet another containment and debridement device according to various aspects of the present disclosure, the device including an internal frame, FIG. 16A is a cross-sectional view of the device, FIG. 16B is a perspective view of the internal frame in an undeformed configuration, FIG. 16C is a top view of the internal frame deformed into an elongated shape, FIG. 16D is a top view of the internal frame deformed into a peanut-shape, and FIG. 16E is a top view of the internal frame deformed into an irregular shape;

FIG. 17 is a perspective view of a containment and debridement device having a substantially frusto-conical shape according to various aspects of the present disclosure;

FIG. 18 is a perspective view of another containment and debridement device according to various aspects of the present disclosure, the device having a substantially frusto-conical portion and a substantially cylindrical portion;

FIG. 19 is a perspective view of yet another containment and debridement device according to various aspects of the present disclosure, the device having a substantially cylindrical shape;

FIG. 20 is a perspective view of yet another containment and debridement device according to various aspects of the present disclosure, the device having a substantially rectangular prism shape;

FIG. 21 is a perspective view of yet another containment and debridement device according to various aspects of the present disclosure, the device having a substantially triangular prism shape;

FIGS. 22A-22D relate to yet another irrigation and debridement assembly according to various aspects of the present disclosure, FIG. 22A is a perspective view of a containment and debridement device of the assembly, the device being in a relaxed position, FIG. 22B is a partial side view of the assembly with the device being in the relaxed position, FIG. 22C is a perspective view of the assembly with the device being in a wrapped position and a first configuration, and FIG. 22D is a partial sectional view of the assembly with the device being in a wrapped position and a second configuration;

FIGS. 23A-23B relate to yet another irrigation and debridement assembly according to various aspects of the present disclosure, FIG. 23A is a perspective view of a containment and debridement device of the assembly in a relaxed position, and FIG. 23B is a partial perspective view of the assembly with the device in the relaxed position; and FIGS. 24A-24B relate to yet another irrigation and debridement assembly according to various aspects of the present disclosure, FIG. 24A is a perspective view of a containment and debridement device of the assembly, the device being in a relaxed position, and FIG. 24B is a partial cross-sectional view of the assembly with the device being in a wrapped position.

Corresponding reference numerals indicate corresponding parts throughout the several views of the drawings.

DETAILED DESCRIPTION

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Any method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

When a component, element, or layer is referred to as being "on," "engaged to," "connected to," or "coupled to" another element or layer, it may be directly on, engaged, connected or coupled to the other component, element, or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various steps, elements, components, regions, layers and/or sections, these steps, elements, components, regions, layers and/or sections should not be limited by these terms, unless otherwise indicated. These terms may be only used to distinguish one step, element, component, region, layer or section from another step, element, component, region, layer or section. Terms such as "first," "second," and other numerical terms when used herein do not imply a sequence or order unless clearly indicated by the context. Thus, a first step, element, component, region, layer or section discussed below could be termed a second step, element, component, region, layer or section without departing from the teachings of the example embodiments.

Spatially or temporally relative terms, such as "before," "after," "inner," "outer," "beneath," "below," "lower," "above," "upper," and the like, may be used herein for ease of description to describe one element or feature's relationship to another element(s) or feature(s) as illustrated in the figures. Spatially or temporally relative terms may be intended to encompass different orientations of the device or system in use or operation in addition to the orientation depicted in the figures.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. For example, "about" may comprise a variation of less than or equal to 5%, optionally less than or equal to 4%, optionally less than or equal to 3%, optionally less than or equal to 2%, optionally less than or equal to 1%, optionally less than or equal to 0.5%, and in certain aspects, optionally less than or equal to 0.1%.

In addition, disclosure of ranges includes disclosure of all values and further divided ranges within the entire range, including endpoints and sub-ranges given for the ranges.

Example embodiments will now be described more fully with reference to the accompanying drawings.

As noted above, wounds are commonly managed using irrigation and debridement. However, many existing irrigation procedures release contaminated irrigation fluid, aerosols, and wound debris into the surrounding environment (e.g., the floor, the air, nearby medical equipment, and healthcare professionals and staff in proximity to the area where the procedures are performed), onto medical personnel, and onto the patient. The release of irrigation fluid and wound debris can lead to health hazards related to microorganism contamination, exposure to healthcare staff, and other environmental hazards, such as pooled water on the floor of a high-traffic area and droplet exposure to reused medical devices and equipment. The environmental hazards frequently necessitate time-consuming clean-up procedures after the irrigation and debridement procedure. Furthermore, many wounds receiving irrigation and debridement treatment are associated with multi-drug-resistant organisms. The Center for Disease Control recommends several precautions for the performance of procedures that could release multi-drug-resistant organisms into the air, such as the use of private medical rooms, limitations on medical personnel present, the use of personal protective equipment for medical personnel, and intense cleaning and disinfecting procedures after the treatment. These time-consuming and often complex requirements may deter medical personnel from performing irrigation and debridement treatments adequately and efficiently. Other aspects of wound irrigation and debridement treatment present different challenges. For example, mechanical debridement of a wound bed without the medical professional's hands while performing concurrent irrigation can lead to accidental sticking of the debridement device to the wound bed and injuries to the medical professional, especially on sharp wound beds such as bony edges and exposed infected structures or hardware.

Additional procedures are available to mitigate the environmental contamination caused by typical irrigation and debridement procedures. One method of reducing environmental contamination is through the use of suction to remove excess irrigation fluid and wound debris. To be effective, suction requires a device to be in direct contact with the wound bed and create an adequate seal with the wound bed. However, achieving constant and direct contact sufficient to minimize contamination is difficult due to typically uneven surfaces of wound beds and rigidity of most suction devices, as well as the inability to apple these rigid structure close to vital organs, such as the heart or major blood vessels. Another method of mitigation is the use of flexible tips for containment of wound debris, and optionally to create a seal for application of suction. However, such tips do not perform well on uneven surfaces. Additionally, the tips inhibit visibility of the wound bed, which can lead to inadequate wound debridement. Yet another method of mitigation is securing a bag around a portion of the patient's body that includes the body area to be treated, or a bag around the irrigation device being used. These procedures are often cumbersome and require long set-up times and unrealistic patient positioning. Furthermore, visibility during irrigation and debridement is reduced, access to the wound site for additional mechanical debridement is limited, and irrigation fluid and wound debris may pool within the bag, limiting the quality and efficiency of the process. Accordingly, improved methods and tools for irrigation and debridement of wound beds would be desirable.

In various aspects, the present disclosure provides an assembly for irrigation of a target body region (e.g., a wound bed), mechanical debridement of the target body region, and containment of irrigation fluid and/or wound debris. In certain aspects, the assembly may be referred to as an "irrigation and debridement assembly" or "assembly." The assembly includes a nozzle that discharges irrigation fluid (e.g., saline or antibiotic solution) to the target body region, and a device that contains the irrigation fluid. In certain aspects, the device may be referred to as a "containment device" or a "containment and debridement device," depending on whether the device includes a debridement region. The device may at least partially surround the nozzle and include an outlet to transfer the irrigation fluid to the target body region. The device includes a compliant region that can maintain contact with the target body region to act as a barrier to the release of irrigation fluid and wound debris. The assembly also includes a debridement region that can selectively debride the target body region, such as by compressing the compliant region of the device. The debridement region may be coupled to at least one of the nozzle or the device. In certain variations, the assembly may also include a vacuum port. Maintaining contact between the compliant region of the device and the target body region may also facilitate the build-up of negative pressure for use of the vacuum port to remove irrigation fluid and/or wound debris. In certain embodiments, the compliant region is porous and capable of absorbing irrigation fluid and/or wound debris.

The assembly and device according to various aspects of the present disclosure can minimize release (e.g., splash, aerosolizing) of the irrigation fluid and wound debris into the surrounding environment, thereby reducing contamination and spread of bacteria. The assembly can be operated by a medical technician using a single hand to increase ease of access to difficult-to-reach wound beds and leave another hand free to perform other tasks. Due to elimination of a bag for containment of irrigation fluid and wound debris, visibility during the procedure is improved compared to other methods of irrigation. The debridement region allows the medical personnel to perform selective physical debridement via the same device as irrigation, without the need for direct contact by the technician (e.g., hand-scrubbing), thereby reducing or avoiding accidental exposures and occupational injuries. The compliant region may reduce suction pressure and resulting sticking to the wound bed.

The containment device can be used with various sizes, shapes, and types of irrigation nozzles and optional vacuum ports, and can be efficiently installed and removed from the nozzle, optionally with customizable positioning. A size and shape of the containment device may be tailored to a particular wound type. In certain variations, the containment device may be disposable. A procedure to use the assembly may be simple, and similar to other existing irrigation tools. Furthermore, a single technician can readily perform both irrigation and mechanical debridement. Additionally, due to the ease of use and decreased environmental contamination, the assembly and device may encourage increased use of irrigation and debridement treatment in locations that would have previously been infeasible, such as ancillary healthcare facilities and homes.

Target Body Regions

The assembly and device according to various aspects of the present disclosure may be used for irrigation and debridement of a target body region (also referred to as a "target region"). As used herein, "target body region" includes wound beds (e.g., pressure sores or tissue damage resulting from a cut, an impact, a burn, or frostbite), surgical sites, skin conditions (e.g., infection), and skin areas to receive hygiene-, cosmetic-, or maintenance-related procedures. The target body region can be on a human or an animal.

Wound Irrigation Systems

Figure 1:
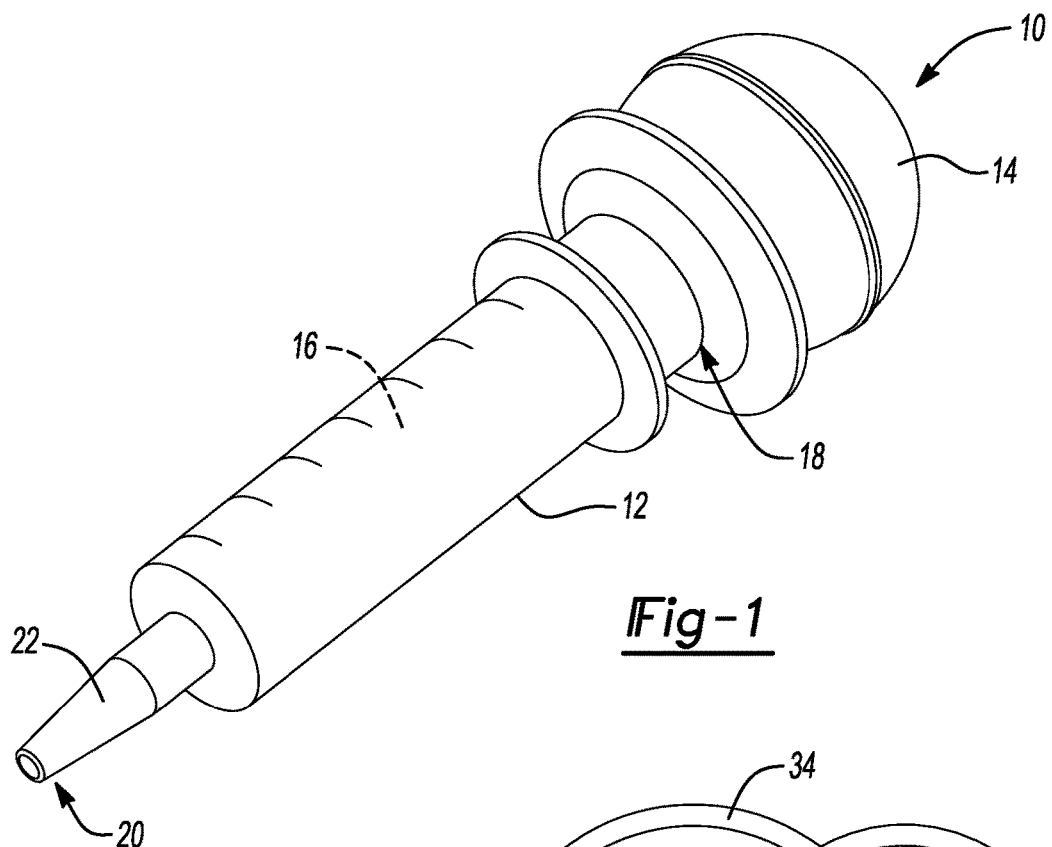
FIG. 1 is a perspective view of a wound irrigation system including bulb syringe.
Figure 2:
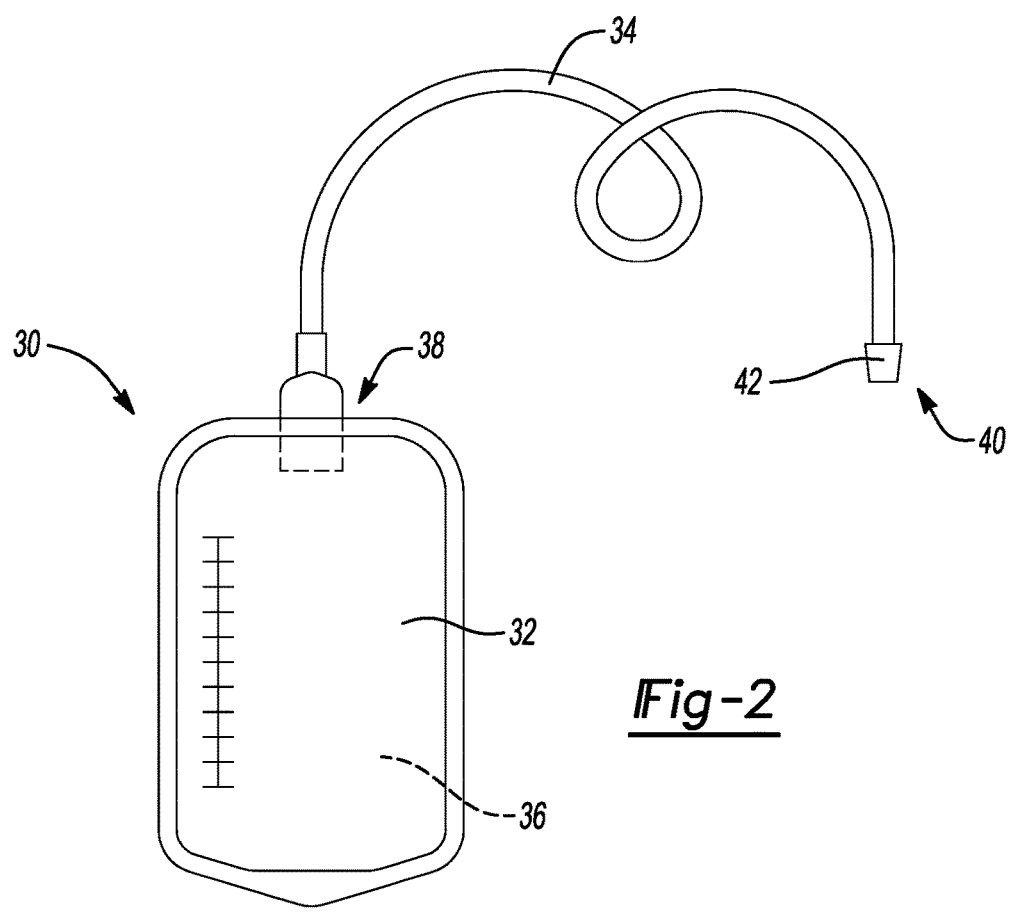
FIG. 2 is a front view of a wound irrigation system including a trans-urethral resection tubing system.

The assembly can include a nozzle from any type of irrigation system. Irrigation systems include low-pressure irrigation systems or high-pressure irrigation systems. Examples of low pressure irrigation systems include bulb-type irrigation systems (see, e.g., FIG. 1) and trans-urethral resection tubing ("TUR") (see, e.g., FIG. 2). An example of a high-pressure irrigation system includes a pulse lavage system (see, e.g., FIG. 3). The nozzle is used to deliver irrigation fluid (e.g., saline solution or antibiotic solution) to the target body region. The irrigation fluid can be discharged in a steady stream, as a pulsed stream, as a mist, or in any other effective manner. Some irrigation nozzles are used in conjunction with suction ports. The nozzle and the suction port may be part of a single device, or they may be separate systems that are used together or sequentially. FIGS. 1-3 depict examples of wound irrigation systems that can be used in an irrigation and debridement assembly according to various aspects of the present disclosure.

With reference to FIG. 1, a bulb-type irrigation system 10 (e.g., an ASEPTO™ syringe) according to various aspects of the present disclosure is provided. The bulb-type irrigation system 10 includes a tube 12 and a bulb 14. The tube 12 includes a fluid reservoir 16, which may be configured to contain an irrigation fluid. The tube 12 extends between a proximal end 18 and a distal end 20. The bulb 14 is coupled to the proximal end 18 of the tube 12 and may be separable from the proximal end 18 of the tube 12. The distal end 20 of the tube 12 includes a nozzle 22. The nozzle 22 is configured to deliver irrigation fluid to a target body region. For example, a medical technician can squeeze the bulb 14 to move irrigation fluid out of the tube 12, through the nozzle 22, and to the target body region. Although the bulb-type irrigation system 10 does not include an integral suction port, it may be used in conjunction with a separate suction port for removal of irrigation fluid and/or wound debris from the target body region.

Referring to FIG. 2, a TUR irrigation system 30 according to various aspects of the present disclosure is provided. The TUR irrigation system 30 includes a bag 32 and a hose 34. The bag 32 includes a reservoir 36 for containment of an irrigation fluid. The hose 34 extends between a proximal end 38 and a distal end 40. The proximal end 38 is coupled to the bag 32. The distal end 40 includes a nozzle 42 for discharging the irrigation fluid to the target body region. The irrigation fluid is drawn out of the bag 32, through the hose 34, and out the nozzle 42 via gravity and/or pressure. Although the TUR irrigation system 30 does not include an integral suction port, it may be used in conduction with a separate suction port for removal of irrigation fluid and/or wound debris from the target body region.

With reference to FIG. 3A, a pulse lavage irrigation system 50 according to various aspects of the present disclosure is provided. The pulse lavage irrigation system 50 includes a handle 52, an outlet tube 54, and an inlet tube 56. The outlet tube 54 includes a nozzle 58 that is configured to discharge irrigation fluid to a target body region. The inlet tube 56 includes a suction port (not shown) that is configured to remove irrigation fluid and debris from the target body region via negative pressure. Distal ends of the outlet and inlet tubes 54, 56 are coupled to a tip 60 and may extend into an interior region of the tip (not shown). In certain aspects, the tip 60 may comprise a flexible material. In certain aspects, the pulse lavage system 50 may include a mechanism, such as a trigger (not shown), that can control a rate that irrigation fluid is discharged from the nozzle 58.

Irrigation and Debridement Assemblies

Referring to FIG. 3B, an irrigation and debridement assembly 70 according to various aspects of the present disclosure is provided. The assembly 70 includes the pulse lavage irrigation system 50 and a containment device 72. The containment device 72 comprises a body 74 that extends along a longitudinal axis 75. The body 74 includes a first or compliant region 76. At least one of the pulse lavage irrigation system 50 and the containment device 72 includes a second or debridement region (not shown; see, e.g., debridement region 154, of FIGS. 4A-4C). The containment device 72 includes an interior region 77, a first opening (not shown) at a distal end 78 of the containment device 72, and a second opening 80 at a proximal end 82 of the containment device 72.

The first opening and the second opening 80 are in fluid communication with the interior region 77. The interior region 77 and the first opening are configured to transfer irrigation fluid to the target body region. The second opening 80 is configured to receive at least a portion of the nozzle 58. The nozzle 58 and the suction port are in fluid communication with the interior region 77.

Irrigation and debridement assemblies according to various aspects of the present disclosure generally include a wound irrigation system and a containment device At least one of the irrigation system and the containment device may include a debridement region for performing mechanical debridement of a target body region. Containment devices according to various aspects of the present disclosure may be used with any suitable wound irrigation system, such as the bulb-type irrigation system 10 of FIG. 1, the TUR irrigation system 30 of FIG. 2, or the pulse lavage irrigation system 50 of FIG. 3. The irrigation system generally includes a nozzle for dispensing irrigation fluid through the containment device and to the target body region. The irrigation system may optionally include a suction port for removal of irrigation fluid and/or wound debris. The suction port may be disposed inside of the containment device, or it may be a separate component that is used in the target body region independent of the nozzle. The nozzle and optional suction port may be used alone, or with a tip (see, e.g., tip 60 of FIG. 3A).

First or Compliant Region

A containment device according to various aspects of the present disclosure includes a compliant region. The compliant region engages the target body region to minimize release of irrigation fluid and/or wound debris from the target body region. Engagement of the compliant region with the target body region can create a fluid seal between a suction port and the target body region to facilitate effective removal of irrigation fluid and/or wound debris from the target body region. The compliant region can compress, bend, or otherwise deform to maintain contact with the target body region during irrigation and debridement. At least a portion of the compliant region is disposed axially between the vacuum port during irrigation and debridement to reduce or prevent sticking of the vacuum port to the target body region. Furthermore, the compliance allows a medical technician to modify an angle and a height of the nozzle and/or vacuum port during irrigation and debridement, while maintaining engagement between the containment device and the target body region. The compliant region may be soft so that it does not damage sensitive portions of the target body region.

In certain variations, the compliant region may comprise a foam, such as a low-density foam, or a foam-like material. In certain variations, the compliant region may comprise a soft silicone or silicone-like material. By way of example, the silicone may have a Shore A hardness of less than or equal to about 10. In certain variations, the compliant region is gel-like and deformable. In certain variations, the compliant region has a bellows or bellows-like design.

In one example, a density of the compliant region is greater than or equal to about 0.5 lb/ft$^3$ to less than or equal to about 20 lb/ft$^3$, optionally greater than or equal to about 0.75 lb/ft$^3$ to less than or equal to about 1.5 lb/ft$^3$, or optionally about 0.85 lb/ft$^3$. The foam may be open-cell foam or closed-cell foam. In some variations, the compliant region comprises an open-cell foam. The open-cell foam may allow irrigation fluid to be absorbed into the compliant region from any direction. The compliant region may comprise a polymer selected from the group consisting of: polyurethane, polyethylene, cellulose, silicone, thermoplastic elastomer, thermoplastic polyurethane, polyvinyl chloride (PVC), and combinations thereof.

In various aspects, the compliant region may be porous. Accordingly, the compliant region may comprise a plurality of pores. The plurality of pores may include a plurality of internal pores and external pores that are open to one another and form continuous flow paths or channels extending from an inlet to an exit. As used herein, the terms "pore" and "pores" refer to pores of various sizes, including so-called "macropores" (pores of greater than 50 nm diameter), "mesopores" (pores having diameter between 2 nm and 50 nm), and "micropores" (pores having diameter of less than 2 nm), where the pore size refers to an average or median value, including both the internal and external pore diameter sizes. The pores may thus be randomly disposed throughout while being interconnected and permitting fluid flow therethrough. In one example, the plurality of pores comprises greater than or equal to about 70% macropores, optionally greater than or equal to about 75% macropores, optionally greater than or equal to about 80% macropores, optionally greater than or equal to about 85% macropores, optionally greater than or equal to about 90% macropores, or optionally greater than or equal to about 95% macropores. In some examples, an average pore diameter is greater than or equal to about 0.05 mm to less than or equal to about 2 mm greater than or equal to about 0.1 mm to less than or equal to about 1.5 mm, optionally greater than or equal to about 0.2 mm to less than or equal to about 1 mm, optionally greater than or equal to about 0.3 mm to less than or equal to about 0.9, optionally greater than or equal to about 0.4 mm to less than or equal to about 0.8 mm, optionally greater than or equal to about 0.5 mm to less than or equal to about 0.7, or optionally about 0.6 mm. In some examples, a porosity is greater than or equal to about 50%, optionally greater than or equal to about 60%, optionally greater than or equal to about 70%, optionally greater than or equal to about 75%, optionally greater than or equal to about 80%, optionally greater than or equal to about 85%, optionally greater than or equal to about 90%. For example, the porosity may be greater than or equal to about 85% to less than or equal to about 95%.

In certain aspects, the compliant region may be non-homogeneous, such that certain portions are more compliant than other portions. A non-homogeneous compliant region may facilitate sequential compression of the different portions. In one example, a non-homogeneous compliant region includes variable porosity, with a more porous portion being configured to compress first, and a less porous portion being configured to compress second. In another example, a non-homogeneous compliant region includes variable density, with a less dense portion being configured to compress first, and a denser portion being configured to compress second. In yet another example, a non-homogeneous compliant region includes variable stiffness, with a less stiff portion being configured to compress first, and a stiffer portion being configured to compress second. In certain aspects, the sequentially-compressible portions may be distributed axially (e.g., such that a distal end of the compliant region compresses first).

Second or Debridement Region

As noted above, the irrigation and debridement assembly includes a debridement region. The debridement region may be coupled to at least one of the nozzle or the containment device. The debridement region may be integrally formed with the nozzle and/or the containment device, or the debridement region may be separately formed and subsequently coupled to the nozzle and/or containment device. As used herein, "coupled" means that the debridement region is associated with the nozzle and/or containment device (e.g., the compliant region). In certain variations, the debridement region may be coupled to nozzle and/or containment device with a fastener, such as hook-and-loop fastener (e.g., VELCRO®), one or more snaps, one or more staples, adhesive (e.g., a flexible adhesive), stitching, any other suitable fastener, or combinations thereof. In certain variations, the debridement region may free of a distinct fastener such that it is coupled to the nozzle and/or containment device by mechanical interlock, friction fit, heat bonding, combinations thereof, or any other suitable method. In certain variations, the debridement region may be directly connected to the nozzle and/or containment device.

In certain variations, the debridement region is coupled to the compliant region of the containment device. In certain aspects, a joint between the debridement region and the compliant region may be compressible, such as when the device includes a flexible adhesive or when the device is free of a distinct fastener. In certain variations, at least a portion of the debridement region or the compliant region may be configured to move with respect to at least a portion of the other of the debridement region or the compliant region (e.g., by compressing the compliant region). For example, the debridement region may be coupled to the compliant region at a discrete axial location (e.g., by an adhesive strip or threads) such that other portions of the debridement and/or compliant regions may slide and/or compress with respect to one another. In certain aspects, the entire debridement region may be configured to move with respect to the compliant region. For example, the debridement region may be disposed within an interior region and configured to translate axially with respect to the compliant region, such as when the debridement region is coupled to the compliant region via a fiction fit.

The debridement region is configured to selectively engage the target body region, such as by compressing the compliant region of the containment device, to mechanically debride the target body region. In certain aspects, the debridement region may also be flexible and/or compressible. Mechanical debridement may be used, for example, to remove dead and non-viable tissue from the target body region.

Compared to the compliant region, the debridement region may have a different stiffness (e.g., a higher stiffness), a different density (e.g., a higher density), a different roughness (e.g., a higher roughness), a different firmness (e.g., a higher firmness), and/or a different compliance (e.g., a lower compliance). The above characteristics may be based on respective bulk structures of the compliant region and the debridement region. In one example, the compliant region has a first stiffness, and the debridement region has a second stiffness that is greater than the first stiffness. The debridement region may comprise a variety of structures and materials to form the requisite composite stiffness.

In certain aspects, compositions of the debridement region and the compliant region may be similar or identical. In one example, the debridement and compliant regions have the same composition, with the debridement region having a lower porosity. In another example, the debridement and compliant regions comprise the same material, with a surface of the debridement region further comprising a rough surface coating, such as a resin with optional abrasive particles. In yet another example, the debridement and compliant regions comprise the same material, and the debridement region has a higher stiffness due to geometries of the respective regions.

In certain variations, the compliant region and the debridement region have similar structures (e.g., open-cell foam), but comprise different materials having corresponding different properties. For example, each material may have a distinct stiffness, density, and/or porosity. The debridement region may comprise a polymer such as cellulose, nylon, polypropylene, silicone, polyurethane, thermoplastic polyurethane, thermoplastic elastomer, PVC, or combinations thereof. In one example, the debridement region comprises a polymer selected form the group consisting of cellulose, nylon, polypropylene, silicone, polyurethane, thermoplastic polyurethane, thermoplastic elastomer, PVC, or combinations thereof.

In certain aspects, the compliant region and the debridement region have distinct structures. In one example, the debridement region comprises a plurality of bristles (e.g., thick silicone bristles, thin nylon bristles, and/or looped bristles) having free ends that are configured to engage the target body region. In other examples, the debridement region comprises a plurality of fibers, such as woven fibers and/or non-woven fibers. In one example, the debridement region comprises a mesh fabric. In yet other examples, the debridement region comprises a foam, such as an open-cell foam and/or a closed cell foam. In yet another example, the debridement region includes a polymer having embedded abrasive particles. In yet other examples, the debridement region comprises a plurality of protrusions that are configured to engage the target body region, such as nubs, spikes, or rollers. In yet other examples, the debridement region comprises a textured surface, defining a plurality of waveforms or ridges. In various aspects, the debridement region comprises at least one of a plurality of bristles, a plurality of protrusions, a plurality of non-woven fibers, a plurality of woven fibers, a mesh, an open cell foam, a closed cell foam, a plurality of particles, or a surface coating.

In certain aspects, distal surface of the debridement region may be recessed with respect to a distal surface of the compliant region so that the compliant region may be compressed to engage the debridement region with the target body region. However, in various alternative aspects, the distal surface of the debridement region may extend past the distal surface of the compliant region, or be disposed substantially flush with respect to the distal surface of the compliant region. The debridement region may comprise a single region (see, e.g., debridement region 154 of FIGS. 4A-4C) or a plurality of regions (see, e.g., debridement regions 372 of FIGS. 9A-9B). The debridement region may define a closed shape having a central opening through which irrigation fluid may flow (e.g., an annular shape). In certain other aspects, the debridement region may define an open shape, such as a U- or C-shaped cross section. In certain aspects, the debridement region includes a plurality of debridement regions having respective distal surfaces that are disposed at different heights with respect to the distal surface of the compliant region, to provide different intensities of mechanical debridement.

In various aspects, a second region may be suitable for a different purpose than debridement or may have additional utility. For example, a second region may reduce or prevent sticking of a suction port and/or tip to a target body region. In certain aspects, the second region may cooperate with a first or compliant region to reduce or prevent sticking. In one example, a distal surface of a second region is substantially planar and smooth such that it would not perform substantial debridement. In another example, a distal surface of a second region defines a circumferential waveform (see, e.g., discussion accompanying FIGS. 7A-7B).

Example Wound Irrigation and Debridement Assemblies

Examples of irrigation and debridement assemblies according to various aspects of the present disclosure are shown in FIGS. 4A-11 and 22A-24B and described below.

Three-Configuration Containment and Debridement Device

With reference to FIGS. 4A-4C, an irrigation and debridement assembly 110 according to various aspects of the present disclosure is provided. The assembly 110 includes a wound irrigation system 112 and a containment and debridement device 114. The wound irrigation system 112 and the device 114 are coupled to one another. The wound irrigation system 112 may be similar to the pulse lavage wound irrigation system 50 of FIGS. 3A-3B. The wound irrigation system 112 may include an outlet tube 116 having a nozzle 118, and an inlet tube 120 having a suction port 122. The nozzle 118 and the suction port 122 may be coupled to a tip 124. The tip 124 may define a passage 125 in fluid communication with the nozzle 118 and the suction port 122 for transferring irrigation fluid.

The device 114 includes a body 126. The body 126 extends along a longitudinal axis 128. The body 126 comprises an interior region or void space 130. The body 126 also defines a distal surface 132 comprising a first opening 134, and a proximal surface 136 defining a second opening 138. The distal surface 132 and the proximal surface 136 may be disposed opposite one another. In some examples, the distal surface 132 and the proximal surface 136 are disposed substantially parallel one another and substantially perpendicular to the longitudinal axis 128. However, in some other examples, one or both of the distal and proximal surfaces 132, 136 is disposed non-perpendicular to the longitudinal axis 128, is curved or contoured, or includes multiple facets.

The body 126 also includes an outer surface 140 and an inner surface 142. The outer and inner surfaces 140, 142 may extend substantially perpendicular to the distal and proximal surfaces 132, 136. In certain variations, the outer and inner surfaces 140, 142 may each be substantially cylindrical. The inner surface 142 at least partially defines the interior region 130 of the body 126. The longitudinal axis 128 may extend through a center of the interior region 130. The first and second openings 134, 138 are fluidly connected to the interior region 130.

The body 126 may comprise a seam 146, which extends radially between the outer and inner surfaces 140, 142, and axially between the distal and proximal surfaces 132, 136. The body 126 may include a first seam surface 148 and a second seam surface 150. The first and second seam surfaces 148, 150 may be separated to place the body 126 in an open configuration, such as during assembly of the device 114 to the nozzle 118 and removal of the device 114 from the nozzle 118. The first and second seam surfaces 148, 150 may engage one another when the body is in a closed configuration, such as during use of the assembly 110.

The device 114 may further comprise a fastener (not shown) to maintain the body 126 in the closed configuration. The fastener may engage the outer surface 140 (see, e.g., peripheral fastener 548 of FIG. 14), the inner surface 142, and/or the first and second seam surfaces 148, 150 (see, e.g., continuous fastener 490 of FIG. 12 and discrete fasteners 520 of FIG. 13). The fastener may comprise a hook-and-loop fastener (e.g., VELCRO®), adhesive, a snap, push connect, a staple, threads (e.g., sewing the device in the closed configuration), a button, a strap, a ratchet, a zipper, a lace, magnets, a combination thereof, or any other suitable fastener.

The body 126 includes a first or compliant region 152 and a second or debridement region 154. Each of the compliant region 152 and the debridement region 154 may define a substantially annular shape, with the compliant region 152 being disposed at least partially outward of the debridement region 154 with respect to the longitudinal axis 128 (e.g., radially outward). The tip 124 of the wound irrigation system 112 engages the inner surface 142 of the body 126 in an interference fit to couple the device 114 to the nozzle 118. More particularly, the tip 124 may engage the compliant region 152. In various alternative aspects, a tip may engage a debridement region (see, e.g., FIG. 22B).

In certain aspects, the compliant region 152 includes the distal surface 132 of the body 126. The compliant region 152 may include a first portion 156 disposed axially between the debridement region 154 and the distal surface 132. The compliant region 152 may define a second portion 158 disposed axially between the nozzle 118 and the debridement region 154.

The debridement region 154 is coupled to an interior surface 155 of the compliant region 152. The inner surface 142 of the body 126 may include at least a portion of the interior surface 155 of the compliant region 152. The debridement region 154 may be fluidly connected to the interior region 130. The debridement region 154 may extend inward toward the longitudinal axis 128. A central opening 160 of the debridement region 154 may be substantially coaxial with the interior region 130 such that the longitudinal axis 128 extends through a center of the central opening 160.

The device 114 can be used in a first configuration (FIGS. 4A-4C), a second configuration (not shown), or a third configuration (not shown), depending on a level of mechanical debridement desired. An intensity of mechanical debridement may increase between the first configuration and the second configuration, and between the second configuration and the third configuration. In general, the compliant region 152 may be axially compressed or expanded to shift the device 114 between the first, second, and third configurations. As will be described in greater detail below, the compliant region 152 defines a first axial dimension 162 in the first configuration, a second axial dimension 164 in the second configuration, and a third axial dimension (not shown) in the third configuration. The second axial dimension 164 is less than the first axial dimension 162, and the third axial dimension is less than the second axial dimension 164.

In the first configuration, the device 114 is primarily used for irrigation. At least a portion of a debridement surface 157 of the debridement region 154 (e.g., substantially the entire debridement surface 157) is axially offset from the distal surface 132 of the body. Accordingly, when the distal surface 132 engages a target body region, the debridement region 154 remains disengaged from the target body region. The debridement surface 157 is axially offset from the distal surface 132 of the body 126. In the first configuration, the compliant region 152 may define the first axial dimension 162 substantially parallel to the longitudinal axis 128. The compliant region 152 may be substantially uncompressed, or minimally compressed such that the distal surface 132 maintains contact with the target body region, while the debridement region 154 remains disengaged from the target body region and the nozzle 118. Depending on the stiffness of the compliant region 152 and a pressure applied by a medical technician, engagement between the distal surface 132 and the target body region may provide gentle mechanical debridement.

In the second configuration, at least the first portion 156 of the compliant region 152 is compressed along the longitudinal axis 128 such that the debridement region 154 engages the target body region to perform mechanical debridement. In certain aspects, in the second configuration, the debridement surface 157 is substantially coplanar from the distal surface 132 of the body 126. The compliant region 152 may define the second axial dimension 164. The second axial dimension 164 is less than or equal to a difference between the first axial dimension 162 and a fourth axial dimension 166 of the first portion 156 of the compliant region 152 (e.g., the second axial dimension 164 may be less than the difference when the debridement region 154 is also axially compressed). In the second configuration, the distal surface 132 remains engaged with the target body region.

In the third configuration, at least the first portion 156 and the second portion 158 of the compliant region 152 are compressed along the longitudinal axis 128 such that the debridement region 154 engages both the target body region and the nozzle 118. In certain configurations, the debridement surface 157 may be substantially coplanar with the distal surface 132 of the body 126. Engagement between the nozzle 118 (e.g., through the tip 124) and the debridement region 154 allows the medical technician to increase an applied force along the longitudinal axis 128, thereby increasing a pressure of the mechanical debridement. In the third configuration, the compliant region 152 may define the third axial dimension. The third axial dimension may be less than or equal to a difference between the first axial dimension 162 and a sum of the fourth axial dimension 166 and a fifth axial dimension 168 of the second portion 158 of the compliant region 152. In the third configuration, the distal surface 132 remains engaged with the target body region.

During use of the assembly 110, the irrigation fluid is transferred from the nozzle 118, through the interior region 130 and the first opening 134 to the target body region. The compliant region 152 may engage the target body region to form a fluid seal and/or facilitate the application of negative pressure (i.e., vacuum) via the suction port 122. The body 126 can be axially compressed between configurations to selectively perform mechanical debridement at varying intensities. Thus, the assembly 110 can be used to perform both irrigation and mechanical debridement. In all three configurations, the suction port 122 and tip 124 remain spaced apart from the target body region to reduce or prevent sticking.

Two-Configuration Containment and Debridement Device

With reference to FIG. 5, another irrigation and debridement assembly 180 according to various aspects of the present disclosure is provided. Unless otherwise described, the assembly 180 may be similar to the assembly 110 of FIGS. 4A-4C. The assembly includes a wound irrigation system 182 and a containment and debridement device 184. The wound irrigation system 182 includes a nozzle 186 and a suction port (not shown). The nozzle 186 is configured to deliver irrigation fluid to a target body region.

The device 184 includes a body 188 extending along a longitudinal axis 190. The body 188 comprises an interior region 192, a first or compliant region 194, and a second or debridement region 196. The compliant region 194 includes a distal surface 198 comprising an opening 200 through which irrigation fluid may be transferred. The debridement region 196 is substantially annular, and is coupled to an inner surface 201 of the compliant region 194. The debridement region 196 engages the nozzle 186. The debridement region 196 is coupled to at least one of the nozzle 186 an the inner surface 201 of the compliant region 194.

The device can be used in a first configuration (FIG. 5) and a second configuration (not shown). In the first configuration, the assembly 180 is used primarily for irrigation. The compliant region 194 defines a first axial dimension 202. The distal surface 198 of the compliant region 194 is configured to engage the target body region. The debridement region 196 is axially offset from the distal surface 198 such that it does not engage the target body region.

In the second configuration, the assembly 180 may be used for mechanical debridement and optional irrigation. In the second configuration, the compliant region 194 is compressed along the longitudinal axis 190 to engage the debridement region 196 with the target body region. The compliant region 194 may be compressed to a second axial dimension 204 less than the first axial dimension 202. A third axial dimension 206 corresponds to a portion 208 of the compliant region 194 disposed axially between the distal surface 198 and the debridement region 196 (i.e., an amount that the debridement region 196 is recessed). The second axial dimension 204 may be less than or equal to a difference between the first axial dimension 202 and the third axial dimension 206. Notably, in the first configuration, the debridement region 196 is axially offset from the target body region by the third axial dimension 206.

Single-Configuration Containment and Debridement Device

Referring to FIGS. 6A-6B, yet another irrigation and debridement assembly 220 according to various aspects of the present disclosure is provided. The assembly 220 may be similar to the assembly 110 of FIGS. 4A-4C unless otherwise described. The assembly 220 includes a wound irrigation system 222 and a containment and debridement device 224. The wound irrigation system 222 includes a nozzle 226 configured to deliver irrigation fluid to a target body region.

The device 224 includes a body 228 extending along a longitudinal axis 230. The body 228 comprises an interior region 232, a first or compliant region 234, and a second or debridement region 236. The compliant region 234 includes a distal surface 238 comprising an opening 240. The interior region 232 and the opening 240 are configured to transfer irrigation fluid from the nozzle 226 to the target body region.

The debridement region 236 has a substantially annular shape. The debridement region 236 is in fluid communication with the interior region 232 of the body 228. The debridement region 236 engages both the nozzle 226 and an interior surface 242 of the compliant region 234. The debridement region 236 is coupled to at least one of the nozzle 226 and the interior surface 242. A debridement surface 244 of the debridement region 236 is disposed substantially flush with the distal surface 238 of the compliant region 234 along the longitudinal axis 230. Accordingly, the device 224 is configured to be operated in a single configuration in which both the debridement region 236 and the compliant region 234 engage the target body region. In various alternative aspects, a single-configuration containment and debridement device includes a debridement region coupled to a distal surface of the compliant region (not shown) rather than an interior surface of the compliant region.

In various aspects, the present disclosure provides another containment device (not shown). The containment device includes a body extending along a longitudinal axis and having a distal surface. The containment device comprises a compliant region and a debridement region. At least a portion of the distal surface of the body comprises the debridement region. The compliant region may be compressed along the longitudinal axis to increase an intensity of debridement.

Nozzle Including Debridement Region

With reference to FIGS. 7A-7B, yet another irrigation and debridement assembly 260 according to various aspects of the present disclosure is provided. The assembly 260 includes an wound irrigation system 262 and a containment device 264. The wound irrigation system 262 includes a nozzle 266 having a second or debridement region 268 coupled to a distal end 269 of the nozzle 266, and a suction port (not shown). The nozzle 266 is configured to discharge irrigation fluid to a target body region. In certain variations, the debridement region 268 comprises a plurality of bristles 270. In various alternative aspects, the second region 268 may define an annular shape having a distal surface that defines a circumferential waveform. The distal surface may reduce or prevent sticking of the nozzle 266 and/or a suction port of the system 262 with the target body region.

The device 264 comprises a body 272 extending along a longitudinal axis 274. The body 272 comprises an interior region 276 and a first or compliant region 278. The compliant region 278 includes a distal surface 280 and an opening 282. The nozzle 266 and the debridement region 268 are disposed at least partially within the interior region 276. The debridement region 268 may engage an interior surface 284 of the interior region 276.

The assembly 260 can be used in a first configuration or a second configuration. In the first configuration, the assembly 260 is primarily used for irrigation. In the first configuration, the debridement region 268 is axially offset from the distal surface 280. The compliant region 278 defines a first axial dimension 286. The distal surface 280 is configured to engage the target body region.

In the second configuration, the compliant region 278 is axially compressed such that the debridement region 268 engages the target body region. The compliant region 278 has a second axial dimension 288 less than the first axial dimension 286. The second axial dimension 288 may be less than or equal to a difference between the first axial dimension 286 and a third axial dimension 290. The third axial dimension 290 corresponds to a portion 292 of the compliant region 278 disposed axially between the distal surface 280 and the debridement region 268. The distal surface 280 may remain in contact with the target body region while the debridement region 268 selectively engages the target body region. A medical technician may increase axial applied force to increase a corresponding pressure of mechanical debridement.

Containment and Debridement Device with Embedded Debridement Region

Referring to FIGS. 8A-8B, yet another irrigation and debridement assembly 310 according to various aspects of the present disclosure is provided. The assembly 310 includes a wound irrigation system 312 and a containment and debridement device 314. The wound irrigation system 312 includes a nozzle 316 configured to deliver irrigation fluid to a target body region. The wound irrigation system 312 may also include a suction port (not shown).

The device 314 comprises a body 318 extending along a longitudinal axis 320. The body 318 comprises an interior region 322, a first or compliant region 324, and a second or debridement region 326. The compliant region 324 includes a distal surface 328. An opening 330 extends into the distal surface 328 and is in fluid communication with the interior region 322. The nozzle 316 is in fluid communication with the interior region 322 such that the interior region 322 and the opening 330 are configured to transfer irrigation fluid to the target body region.

The compliant region 324 also includes a cavity 332 extending into the distal surface 328. The cavity 332 is disposed outward of the interior region 322 with respect to the longitudinal axis 320 (e.g., radially outwardly). In certain aspects, the cavity 332 may be substantially annular.

The debridement region 326 may be disposed within the cavity 332. The debridement region 326 may define a substantially annular shape. However, in various alternative aspects, the debridement region 326 may define other shapes (e.g., a plurality of discrete debridement regions, see, e.g., FIGS. 9A-9B). In certain aspects, the debridement region 326 may be disposed outward of the nozzle 316 with respect to the longitudinal axis 320 such that the nozzle 316 cannot engage the debridement region 326 during axial compression of the compliant region 324

The assembly 310 may be configured to be used in a first configuration and a second configuration. In the first configuration, the assembly 310 is primarily used for irrigation. The compliant region 324 defines a first axial dimension 334. The distal surface 328 is configured to engage the target body region. The debridement region 326 is axially offset from the distal surface 328.

In the second configuration, the assembly 310 may be used for mechanical debridement. The compliant region 324 is axially compressed such that the debridement region 326 engages the target body region. The compliant region 324 defines a second axial dimension 336. The second axial dimension 336 is less than or equal to a difference between the first axial dimension 334 and a third axial dimension 338. The third axial dimension 338 corresponds to a portion 340 of the compliant region 324 disposed axially between the debridement region 326 and the distal surface 328. In the second configuration, the distal surface 328 can remain engaged with the target body region while the debridement region 326 selectively engages the target body region via axial compression.

Containment and Debridement Device with Discrete Debridement Regions

With reference to FIGS. 9A-9B, yet another irrigation and debridement assembly 350 according to various aspects of the present disclosure is provided. Unless otherwise described, the assembly 350 may be similar to the assembly 110 of FIGS. 4A-4C. The assembly 350 includes a wound irrigation system 352 and a containment and debridement device 354. The wound irrigation system 352 includes a nozzle 356 configured to deliver irrigation fluid to a target body region.

The device 354 comprises a body 358 extending along a longitudinal axis 360. The body 358 comprises an interior region 362, a first or compliant region 364, and a second or debridement region 366. The compliant region 364 includes a distal surface 368 having an opening 370. The opening 370 is in fluid communication with the interior region 362. The nozzle 356 is in fluid communication with the interior region 362 such that the interior region 362 and the opening 370 are configured to transfer irrigation fluid to the target body region.

The debridement region 366 comprises a plurality of discrete debridement regions or elements 372. Each debridement element 372 may be coupled to an interior surface 374 of the compliant region 364. The debridement elements 372 are distributed about the longitudinal axis 360. In certain variations, each debridement element 372 is substantially the same distance (e.g., radius) from the longitudinal axis 360 as the other debridement elements 372. Thus, the debridement elements 372 may be distributed in an annular configuration. In certain variations, the debridement elements 372 may be substantially equally spaced about the longitudinal axis 360. In certain other variations, discrete debridement elements may be non-uniformly distributed about a longitudinal axis.

The assembly 350 may be configured to move through first, second, and third configurations in a manner similar to the assembly 110 of FIGS. 4A-4C. In various alternative aspects, a debridement region may comprise a plurality of discrete debridement elements having other arrangements. In one example, discrete debridement elements are embedded in a compliant region (e.g., similar to the debridement region 326 of FIGS. 8A-8B). In another example, a debridement region may comprise a plurality of discrete debridement elements that are coupled to and/or engage a nozzle (e.g., similar to the debridement region 196 of FIG. 5). In another example, a debridement region may comprise a plurality of discrete debridement elements that extend axially between a nozzle and a distal surface of a compliant region (e.g., similar to the debridement region 236 of FIGS. 6A-6B). In yet another example, discrete debridement elements are disposed at different distances from a longitudinal axis (e.g., different radial locations), and/or different axial locations (e.g., different heights) with respect to one another. Furthermore, discrete debridement elements could define different shapes, such as a shape that tapers toward a distal end (e.g., pointed).

Containment and Debridement Device with Multi-Intensity Debridement

In various aspects, a debridement region of a wound irrigation assembly may be configured to provide different intensities of debridement. The debridement region may define a first portion disposed at a first axial distance from a distal surface of a compliant region, and a second portion disposed at a second distinct axial distance from the distal surface. A medical technician can selectively modify the intensity of mechanical debridement by changing an applied axial force to engage (1) neither of the first portion and the second portion, (2) one of the first portion and the second portion, or (3) both of the first portion and the second portion. The debridement region may be compliant such that can compress axially.

Containment and Debridement Device with Connecting Region

In certain aspects, a body according to various aspects of the present disclosure may consist essentially of an interior region, a compliant region, and a debridement region. However, in various alternative aspects, a body may further include one or more additional regions, such as a connecting region. Referring to FIG. 10, an irrigation and debridement assembly 410 according to various aspects of the present disclosure is provided. Unless otherwise described, the assembly 410 may be similar to the assembly 110 of FIGS. 4A-4C. The assembly 410 includes a wound irrigation system 412 and a containment and debridement device 414. The wound irrigation system 412 includes a nozzle 416 configured to discharge irrigation fluid to a target body region.

The device 414 comprises a body 418 extending along a longitudinal axis 420. The body 418 comprises an interior region 422, a first or compliant region 424, a second or debridement region 426, and a connecting region 428. The compliant region 424 may extend axially between a distal surface 430 of the body 418 and a nozzle surface 432. Accordingly, the body 418 is compressible to selectively engage the debridement region 426 with the target body region, and to selectively engage the nozzle 416 with the debridement region 426. The connecting region 428 may be disposed axially between the nozzle surface 432 and a proximal surface 434 of the body 418.

The connecting region 428 may comprise any suitable material for coupling the device 414 to the wound irrigation system 412. In one example, the connecting region 428 comprises a substantially rigid material, such as a substantially rigid thermoplastic material. In another example, the connecting region 428 comprises an elastomer to improve engagement and fluid sealing between the nozzle 416 and the device 414. In yet another example, the connecting region 428 comprises a transparent material to improve visibility of the target body region when a medical technician operates the assembly 410.

With reference to FIG. 11, yet another irrigation and debridement assembly 440 according to various aspects of the present disclosure is provided. Unless otherwise described, the assembly 440 may be similar to the assembly 410 of FIG. 10. The assembly 440 includes a wound irrigation system 442 and a containment and debridement device 444. The wound irrigation system 442 includes a nozzle 446 configured to discharge irrigation fluid to a target body region.

The device 444 includes a body 448 extending along a longitudinal axis 450. The body 448 comprises an interior region 452, a first or compliant region 454, a second or debridement region 456, and a connecting region 458. The compliant region 454 extends axially between a distal surface 460 of the body 448 and a debridement surface 462 of the debridement region 456, such that the compliant region 454 can be axially compressed to selectively engage the debridement region 456 with the target body region.

The connecting region 458 extends axially between the debridement surface 462 and a proximal surface 464 of the body 448. In certain variations, the connecting region 458 may be substantially incompressible such that the device 480 can be used in first and second configurations, but not in a third configuration wherein the nozzle engages the debridement region. In certain alternative embodiments, a debridement region may be in constant engagement with a nozzle or coupled to the nozzle (such as in the device 224 of FIGS. 6A-6B).

The assembly 440 may further comprise a sealing ring 466 disposed at a joint between an outlet tube 468 of the nozzle 446 and the connecting region 458 of the device 444. The sealing ring 466 may improve a fluid seal at the joint. Similar sealing rings may be used on the other devices described herein.

Wrap-Around Containment and Debridement Devices

Containment and debridement devices according to various aspects of the present disclosure may be fabricated in substantially the desired shape (e.g., cylindrical), while being flexible enough to permit coupling to a wound irrigation system. The devices may be referred to as "pre-shaped" containment and debridement devices. In certain aspects, containment regions of pre-shaped devices are free of substantial compressive or tensile stresses.

In various alternative aspects, containment and debridement devices may be fabricated as substantially planar structures or including one or more substantially planar portions. Such devices may be movable between a relaxed or unassembled position to a wrapped or assembled position. In the wrapped position, the device may be wrapped around a portion of a wound irrigation system. Accordingly, the devices may be referred to as "wrap-around" containment and debridement devices.

Wrap-around devices may be fabricated in the relaxed position and therefore manufacturing may be simplified compared to fabrication of pre-shaped devices. In the wrapped position, a compliant region may be subject to compressive and/or tensile stresses (e.g., compressed radially inward regions). A device may be retained in the wrapped position by an external force, such as a fastener, and automatically return to the relaxed position absent the external force. Although the containment and debridement devices described above (e.g., in the discussions accompanying FIGS. 4A-11) are shown as pre-shaped devices, they may alternatively be fabricated as wrap-around devices. Examples of additional wrap-around devices are described below.

With reference to FIG. 22A, a wrap-around containment and debridement device 810 according to various aspects of the present disclosure is provided. The device 810 includes a first or compliant region 812 and a second or debridement region 814. The debridement region 814 is coupled to the compliant region 812. Both the compliant and debridement regions 812, 814 are flexible such that the device 810 can be moved from a relaxed or unassembled position (FIGS. 22A-22B) to a wrapped or assembled position (FIGS. 22C-22D).

In the relaxed position, the compliant region 812 may be substantially planar. The complaint region 812 may include a first surface 816 and a second surface 818 disposed opposite the first surface 816. When the device 810 is in the relaxed position, both of the first and second surfaces 816, 818 are substantially planar. When the device 810 is in the wrapped position, the first surface 816 may be an interior surface and the second surface 818 may be an exterior surface.

The debridement region 814 is coupled to the first surface 816 of the compliant region 812. The debridement region 814 may be non-coextensive with the compliant region 812. For example, the debridement region 814 may have a first width 820 that is smaller than a second width 822 of the complaint region 812 in the relaxed position so that the debridement region 814 has a smaller radius than the compliant region 812 in the wrapped position.

The debridement region 814 may include a main portion 830 and a flange portion 832. In the relaxed position, both the main portion 830 and the flange portion 832 are substantially planar. The flange portion 832 may have a first height 834 that is greater than a second height 836 of the main portion 830 in the relaxed position. In the wrapped position, the flange portion 832 extends radially inward of the main portion 830.

With reference to FIGS. 22B-22D, the device 810 is configured to be coupled to a wound irrigation system 838 to form an irrigation and debridement assembly 840. FIG. 22B depicts the device 810 in the relaxed position prior to being coupled to the wound irrigation system 838. FIGS. 22C-22D show the device 810 in the wrapped position. The wound irrigation system 838 may comprise an outlet tube 842 (FIG. 22B) including a nozzle 844 (FIG. 22C) and an inlet tube 846 (FIG. 22B) including a suction port 848. The nozzle 844 and the suction port 848 may be coupled to a tip 850 and in fluid communication with a passage 851 through the tip 850. When the device 810 is coupled to the wound irrigation system 838, a bottom surface 852 of the tip 850 may engage the flange portion 832 of the device 810 and a side surface or periphery 854 of the tip 850 may engage the main portion 830 of the device 810.

The compliant region 812 may further include a third surface 856 and a fourth surface 858. When the device 810 is in the relaxed position, the fourth surface 858 may be disposed opposite the third surface 856. When the device 810 is in the wrapped position, the third and fourth surfaces 856, 858 may be coupled to one another at a seam 860. For example, the device 810 may include one or more fasteners 862 coupled to the third surface 856 and/or the fourth surface 858. The fastener 862 may include any of the fasteners described herein (see discussion accompanying FIGS. 4A-4C), such as hook-and-loop fastener or an adhesive strip, by way of example. Additionally or alternatively, an inner debridement surface 863 may include a fastener, such as adhesive.

In the wrapped position (FIG. 22C), the device 810 may be wrapped around the tip 850 to form a substantially cylindrical shape, which may be referred to as a body. The first surface 816 may define an interior region 864 (similar to the interior region 130 of FIG. 4A) of the body. The main portion 830 of the debridement region 814 may engage the tip 850. In certain aspects, the debridement region 814 may engage the tip 850 in an interference fit to retain the device 810 on the wound irrigation system 838. The debridement region 814 extends around at least a portion of the periphery 854 of the tip 850.

The device 810 may extend along a longitudinal axis 865 (FIG. 22D) between a fifth or proximal surface 866 and a sixth or distal surface 868. The distal surface 868 may be configured to define an opening 869 (similar to the opening 134 of FIG. 4A) through which irrigation may be transferred in the wrapped position. The distal surface 868 is configured to engage the target body region. In the wrapped position, the device 810 includes an interior region or void space (not shown) that may be similar to the interior region 130 of the device 114 (see FIG. 4A).

The assembly 840 can be used in a first configuration (a first assembled configuration), as shown in FIG. 22C or a second configuration (a second assembled configuration), depending on a desired level of mechanical debridement of the target body region. Intensity of mechanical debridement may increase between the first configuration and the second configuration. The first and second configurations may be similar to the first and second configurations of the device 184 of FIGS. 5A-5B. More particularly, in the first configuration, at least a portion of the debridement region 814 (e.g., substantially the entire debridement region) is recessed with respect to the distal surface 868 and spaced apart from the target body region. In the second configuration, the device 810 is axially compressed such the debridement region 814 engages the target body region. In certain aspects, in the second configuration, the distal surface 868 of the compliant region 812 and a debridement surface 870 of the debridement region 814 cooperate to define a contact surface 872 (FIG. 22D). The contact surface 872 is configured to engage a least a portion of the target body region. In some examples, the sixth surface 868 may be coplanar with the debridement surface 870. In both the first and second configurations, both the suction port 848 and the bottom surface 852 of the tip 850 remain spaced apart from the target body region to reduce or prevent sticking.

In various aspects, the present disclosure provides a method of assembling the irrigation and debridement assembly 840. The method generally includes providing the device 810 having a substantially planar structure or portion. The method further includes engaging the tip 850 of the wound irrigation system 838 with the debridement region 814. For example, the tip 850 may engage the flange portion 832 of the debridement region 814. The method further includes wrapping the device 810 circumferentially around at least a portion of the wound irrigation system 838. The method further includes coupling the device 810 to the wound irrigation system 838. Coupling the device 810 to the wound irrigation system 838 may include coupling the third and fourth surfaces 856, 858 to one another, such as via the fastener 862, to form the seam 860. Coupling the device 810 to the wound irrigation system 838 may include forming an interference fit between the device 810 and the tip 850.

Referring to FIG. 23A, yet another containment and debridement device 880 according to various aspects of the present disclosure is provided. Unless otherwise described, the device 880 may be similar to the device 810 of FIGS. 22A-22C. The device 880 is movable between a relaxed or unassembled position and a wrapped or assembled position. The device 880 includes a first or compliant region 882 and a second or debridement region 884.

The compliant region 882 includes a first surface 886 and a second surface 888 opposite the first surface 886. When the device 880 is in the wrapped position, the first surface 886 may be an interior surface and the second surface 888 may be an exterior surface. The compliant region 882 includes a main portion 890 and one or more projection portions 892. In the relaxed configuration, the main portion 890 and the projection portions 892 are substantially planar. When the device 880 is in the wrapped position, the projection portions 892 are disposed radially inward of the main portion 890. In the example shown, the device 880 includes two projection portions 892, each having a substantially rectangular prism shape. The projection portions 892 are separated by a first channel 894, which may be an axial channel.

The debridement region 884 is coupled to the compliant region 882. When the device 880 is in the wrapped position, the debridement region 884 is disposed radially inward of the projection portions 892 of the compliant region 882. In certain aspects, the debridement region 884 and the projection portions 892 may have substantially the same height perpendicular to the main portion 890 of the compliant region 882. A second channel 896 may be defined between the debridement region 884 and the projection portions 892 of the compliant region 882.

Referring to FIG. 23B, an irrigation and debridement assembly 900 including the device 880 and a wound irrigation system 902 is provided. The device 880 is shown in the relaxed position. The wound irrigation system 902 may be at least partially disposed in the first and second channels 894, 896. A distal end 904 of a tip 906 of the wound irrigation system 902 may be disposed in the second channel 896.

The device 880 may be coupled to the wound irrigation system 902 in a similar manner as described above with respect to the irrigation and debridement assembly 840 of FIGS. 22B-22C. For example, with the tip 906 positioned as described above, the device 880 is wrapped around a portion of the wound irrigation system 902, with third and fourth surface 908, 910 of the device 880 being coupled to one another with a suitable fastener (see, e.g., fastener 862 of FIGS. 22A-22B). Additionally or alternatively, at least a portion of an inner surface 911 of the projection portions 892 (e.g., substantially the entire inner surface 911) may include a fastener, such as adhesive. Accordingly, the device 880 is placed in the wrapped position.

In the wrapped position, the device 880 may have a substantially cylindrical structure and extend between fifth and sixth opposing surfaces 912, 914. The fifth surface 912 may be a proximal surface and the sixth surface 914 may be a distal surface. The assembly 900 may be used in a first configuration or a second configuration. The first and second configurations may be similar to the first and second configurations of the device 184 of FIGS. 5A-5B. In certain aspects, the projection portions 892 may engage the tip 906 in the wrapped position to reduce or prevent movement of the device 880 with respect to the wound irrigation system 902 during use of the assembly 900. In the second configuration the distal end 904 of the tip 906 engages the debridement region 884.

With reference to FIG. 24A, yet another containment and debridement device 940 according to various aspects of the present disclosure is provided. Unless otherwise described, the device 940 may be similar to the device 880 of FIGS. 23A-23B. The device 940 is movable between a relaxed or unassembled position and a wrapped or assembled position. The device 940 includes a first or compliant region 942 and a second or debridement region 944.

The compliant region 942 includes a main portion 946 and one or more projection portions 948. The main portion 946 and the projection portions 948 may be substantially planar when the device 940 is in the relaxed position. In certain aspects, each of the projection portions 948 may include tapered distal surfaces 950. In the example shown, the device 940 includes two projection portions 948 that are separated by a first channel 952, which may be an axial channel.

The debridement region 944 is coupled to the compliant region 942. The debridement region 944 may define an undercut 954. The undercut 954 of the debridement region 944 may cooperate with the tapered distal surfaces 950 of the projection portions to at least partially define a second channel 956.

Referring to FIG. 24B, an irrigation and debridement assembly 960 according to various aspects of the present disclosure is provided. The device 940 is shown in the wrapped position and coupled a wound irrigation system 962. The wound irrigation system 962 includes a tip 964 having a circumferential flange 966 disposed at a distal end 967 of the tip 964.

The wound irrigation system 962 may be at least partially disposed in the first and second channels 952, 956. In certain aspects, the flange 966 may be at least partially disposed in the undercut 954 of the second channel 956. In the example shown, a shape of the undercut 954 is not complementary to the flange 966; however, in other examples, an undercut may be shaped to be complementary to a portion of a wound irrigation system, such as a tip. A portion of the debridement region 944, such as a lip 968, is disposed at least partially within a passage 970 of the tip 964. In various alternative aspects, instead of the undercut 954, a debridement region may be similar to the debridement region 884 of FIGS. 23A-23B, with a portion (e.g., an upper portion closest to the tip) of the debridement region remaining uncoupled to the compliant region to receive a tip.

The device 940 may be coupled to the wound irrigation system 962 in a similar manner as described above with respect to the irrigation and debridement assembly 840 of FIGS. 22B-22C. For example, with the tip 964 being positioned within the second channel 956, the device 940 is wrapped around a portion of the wound irrigation system 962, with third and fourth surfaces 972, 974 of the device 940 being coupled to one another. In certain aspects, the tapered distal surfaces 950 may complement an outer surface of the tip 964. Accordingly, the device 940 is placed in the wrapped position.

In the wrapped position, the device 940 may have a substantially cylindrical structure and extend between fifth and sixth opposing surfaces 976, 978. The fifth surface 976 may be a proximal surface and the sixth surface 978 may be a distal surface. The assembly 960 may be used in a first configuration and a second configuration. The first and second configurations may be similar to the first and second configurations of the device 184 of FIGS. 5A-5B. In certain aspects, the projection portions 948 may engage the tip 964 in the wrapped position to reduce or prevent movement of the device 940 with respect to the wound irrigation system 962 during use of the assembly 960. In the second configuration, the distal end 967 of the tip 964 engages the debridement region 944. Mechanical engagement of the tip 964 with the lip 968 may prevent the flange 966 from projecting axially past the debridement region 944 in a direction 980.

Containment Device—Other Features and Characteristics
Fasteners

In certain aspects, a containment device is compliant enough to be stretched over a nozzle of a wound irrigation system. However, in various alternative aspects, a device includes a seam (see, e.g., seam 146 of FIGS. 4A-4C) that can be placed into an open configuration to assemble the device to a wound irrigation system, or remove the device from the wound irrigation system. The seam may be maintained in the closed configuration by one or more fasteners. The fastener may permanently or removably couple the device to the wound irrigation system. The fastener generally engages a body of the device. Some fasteners advantageously facilitate quick and/or simple assembly and disassembly with the wound irrigation device, such as one-handed assembly. In certain aspects, the fastener is flexible so that it does not interfere with axial compression of the device. Example fasteners are shown in FIGS. 12-14 and described below.

Referring to FIG. 12, an axial cross-sectional view of a containment and debridement device 480 according to various aspects of the present disclosure is provided. The device 480 comprises a body 482 extending along a longitudinal axis 484. The body 482 includes a seam 486 similar to the seam 146 of FIGS. 4A-4C. A pair of seam surfaces 488 (similar to the first and second seam surfaces 148, 150 of FIGS. 4A-4C) may come together when the seam 486 is in a closed configuration. One or both of the seam surfaces include a continuous fastener 490 or are otherwise coupled. Continuous fasteners may include an adhesive, hook-and-loop fastener, or one or more laces or threads, by way of example. The continuous fastener 490 may extend in a substantially axial direction. The continuous fastener 490 may be concealed when the seam 486 is in a closed configuration. Additionally or alternatively, the device 480 may include a fastener, such as adhesive (e.g., a flexible adhesive), on a portion of an interior surface 492 of the device 480.

With reference to FIG. 13, an axial cross-sectional view of another containment and debridement device 510 according to various aspects of the present disclosure is provided. The device 510 comprises a body 512 extending along a longitudinal axis 514. The body 512 includes a seam 516. A pair of seam surfaces 518 come together when the seam 516 is in a closed configuration. One or both of the seam surfaces 518 are coupled or include a plurality of discrete fasteners 520, such as adhesive regions, pieces of hook-and-loop fastener, staples, magnets, snaps, push connects, buttons, or a combination thereof. The use of the plurality of discrete fasteners 520 may improve compressibility of the device 510 compared to the device 480 having the continuous fastener 490 (FIG. 12). Furthermore, decreased stress during compression reduces a chance of the body 512 inadvertently opening at the seam 516.

Referring to FIG. 14, yet another containment and debridement device 540 according to various aspects of the present disclosure is provided. The device 540 includes a body 542 extending along a longitudinal axis 544. The body 542 includes a seam 546. The seam 546 can be maintained in a closed configuration with one or more peripheral fasteners 548, such as straps or ties, hook-and-loop strips, ratchets, or tape. The peripheral fasteners 548 engage an outer surface 550 of the body 542. The peripheral fasteners 548 can be tightened to decrease a dimension (e.g., a radial dimension) of the body 542 such that the device 540 can accommodate different sizes and shapes of wound irrigation systems.

Outer Layer

Some containment and debridement devices according to various aspects of the present disclosure include an outer layer, such as an impermeable outer layer. With reference to FIG. 15, yet another containment and debridement device 560 according to various aspects is provided. The device 560 includes a body 562 extending along a longitudinal axis 564. The body 562 comprises an interior region 565, a first or compliant region 566, and a second or debridement region 568. The debridement region 568 is coupled to an interior surface 570 of the compliant region 566. The body 562 further comprises an outer layer 572 that is disposed along an exterior surface 574 of the compliant region 566. The outer layer 572 may be substantially impermeable to fluids. In certain aspects, the outer layer 572 may be substantially non-porous. Accordingly, as the compliant region 566 absorbs irrigation fluid and/or wound debris, the outer layer 572 retains the irrigation fluid and/or wound debris within the device 560 rather than releasing it to surrounding areas. Additionally, the outer layer 572 may focus vacuum power from the suction port inward to facilitate more efficient removal of the irrigation fluid and/or wound debris from the target body region.

In various alternative aspects, an outer layer may have regions with differing levels of permeability. For example, the outer layer formed from an impermeable material may define interruptions in impermeability. These interruptions can be in the form of, for example, slits or cutouts in the impermeable material. The interruptions may act to focus vacuum power from the suction port radially inward to facilitate more efficient removal of the irrigation fluid and/or wound debris from the target body region while still allowing compliant region 566 to absorb fluid through the exterior surface 574 towards the interior surface 570.

Frame

With reference to FIGS. 16A-16E, in various aspects, the present disclosure provides a containment and debridement device 590 having a reconfigurable shape such that it is customizable based on characteristics of a target body region. The device 590 includes a body 592 extending along a longitudinal axis 594. The body 592 comprises an interior region 596, a first or compliant region 598, and a second or debridement region 600.

The device 590 further comprises an frame 602. The frame 602 comprises a ductile material that can be deformed and maintain a deformed shape. The frame 602 may define a closed curve (e.g., a ring). The frame 602 is coupled to the compliant region 598. For example, the frame 602 is embedded within the compliant region 598 and disposed outward of the interior region 596 with respect to the longitudinal axis 594. However, in various alternative aspects, the frame may be coupled to an exterior surface 604 of the compliant region 598.

The frame 602 may be movable between an undeformed configuration (FIGS. 16A-16B) and various deformed configurations (FIGS. 16C-16E). As best shown in FIG. 16B, in the undeformed configuration, the frame 602 may have a ring shape. Referring to FIG. 16C, the frame 602 is shown in a stretched or elongated configuration. In the elongated configuration, the frame 602 defines a first dimension 606 that is greater than a substantially perpendicular second dimension 608. With reference to FIG. 16D, the frame 602 defines a peanut shape, having a third dimension 610 that is less than substantially parallel fourth and fifth dimensions 612, 614. Referring to FIG. 16E, the frame 602 defines an irregular shape that is tailored to a shape of a particular target body region.

Size and Shape

Containment devices according to various aspects of the present disclosure can be a variety of shapes and sizes, depending on the wound irrigation device to which they are coupled, and the target body region with which they will interact. In certain variations, the containment device is configured to work in conjunction with a handheld wound irrigation device. In certain variations, the containment device is configured to engage a substantial portion of a large body part, such as a leg. An outer dimension (e.g., diameter) of a containment device may be greater than or equal to about 2 cm to less than or equal to about 50 cm, optionally greater than or equal to about 5 cm to less than or equal to about 20 cm (e.g., 10 cm). In one example, the outer dimension is 6 cm and a dimension of an opening to transfer irrigation fluid (e.g., first opening) is about 3 cm. A portion of a compressible region between a debridement region and a distal surface may be greater than or equal to about 0.25 inches to less than or equal to about 2 inches, optionally greater than or equal to about 0.5 inches to less than or equal to about 1.5 inches, or optionally about 1 inch. However, in certain other embodiments, a portion of a debridement region extends beyond a distal surface of a compliant region. In still other embodiments, a debridement region may be disposed on a distal surface of a compliant region. In certain variations a containment device may have a shape tailored to the particular application (see, e.g., FIGS. 16A-21). For example, a containment device configured to be used in a small area, such as behind an ear, may be wedge-shaped. In another example, a containment device configured to engage an elongated region of a body may itself have an elongated shape. Examples of device shapes according to various aspects of present disclosure are depicted in FIGS. 17-21.

FIG. 17 shows a containment and debridement device 630 according to various aspects of the present disclosure. The device 630 includes a body 632 extending along a longitudinal axis 634 between a distal surface 636 and a proximal surface 638. A dimension 640 (e.g., diameter) of the body 632 increases from the proximal surface 638 to the distal surface 636. In certain aspects, the body 632 defines a substantially frusto-conical shape. The body 632 defines a substantially circular cross section in a direction substantially perpendicular to the longitudinal axis 634.

FIG. 18 shows a containment and debridement device 650 according to various aspects of the present disclosure. The device 650 includes a body 652 extending along a longitudinal axis 654 between a distal surface 656 and a proximal surface 658. The body 652 comprises a first portion 660 and a second portion 662. The first portion 660 includes the distal surface 656, and the second portion 662 includes the proximal surface 658. The first portion 660 has a substantially cylindrical shape. The second portion 662 has a substantially frusto-conical shape increasing in diameter from the proximal surface 658 toward the distal surface 656. Both the first portion 660 and the second portion 662 define substantially circular cross sections in a direction substantially perpendicular to the longitudinal axis 654.

FIG. 19 shows a containment and debridement device 670 according to various aspects of the present disclosure. The device 670 includes a body 672 extending along a longitudinal axis 674 between a distal surface 676 and a proximal surface 678. The body 672 defines a substantially cylindrical shape, with a substantially circular cross section in a direction substantially perpendicular to the longitudinal axis 674.

FIG. 20 shows a containment and debridement device 690 according to various aspects of the present disclosure. The device 690 includes a body 692 extending along a longitudinal axis 694 between a distal surface 696 and a proximal surface 698. The body 692 defines a substantially rectangular prism shape, with a substantially rectangular (e.g., square) cross section in a direction substantially perpendicular to the longitudinal axis 694.

FIG. 21 shows a containment and debridement device 710 according to various aspects of the present disclosure. The device 710 includes a body 712 extending along a longitudinal axis 714 between a distal surface 716 and a proximal surface 718. The body 712 defines a substantially triangular prism shape, with a substantially triangular cross section in a direction substantially perpendicular to the longitudinal axis 714.

Joint Between Containment Device and Wound Irrigation System

A containment device according to various aspects of the present disclosure is removably or permanently coupled to the nozzle. In certain aspects, a body of a containment device extends around at least a portion of an outer surface of a nozzle (e.g., around a circumference of the nozzle). In certain aspects, a containment device is coupled to a distal end of a nozzle.

A position of a containment device with respect to a nozzle may be adjustable along a longitudinal axis of the containment device. The position of the containment device on the nozzle affects the distance between an outlet of the nozzle and the target body region. It may be desirable to modify the distance based sensitivity of the target body region, condition of the target body region, desired pressure, or preference of the medical technician. The containment device may include features to facilitate adjustment of its position with respect to the nozzle. For example, in inner surface of the body, may define grooves or other features at sequential predetermined axial locations.

In certain aspects, the containment device may be coupled to the nozzle such that a fluid seal is formed at a joint (e.g., the second opening 80 of the containment device 72 of FIG. 3B). A fit between the containment device and the nozzle may be an interference fit or a press fit, by way of example. A tight seal may minimize vacuum loss when the containment device is used in conjunction with a suction port. An opening of the containment device at the joint may define a variety of shapes (e.g., defining an oval, circle, rectangular, or triangular cross section) and sizes, depending on the shape and size of the nozzle and optional suction port. A surface of the opening may include additional features to improve engagement with the nozzle, such as a plurality of ribs or compression notches. The joint may include the compliant region. In certain aspects, the joint may include a clamp to improve engagement with the nozzle. By way of example, the clamp may comprise metal or plastic.

A nozzle according to various aspects of the present disclosure may be used with or without a tip, such as the tip 60 of the pulse lavage system 50 of FIG. 3A. Additionally or alternatively, the nozzle may be used with a fluid port that is coupled to the nozzle or a containment device. The fluid port may be used to adjust flow characteristics of the irrigation fluid, such as trajectory or flow rate.

As previously noted, a wound irrigation system may optionally include a suction port. The suction port may be in fluid communication with an interior region of a body of a containment device (see, e.g., suction port 122 of FIGS. 4A-4C). In other aspects, an outlet tube including a suction port may be separable from a wound irrigation system. The suction port may be disposed within an interior region of a containment device, or outside an interior region of the containment device. In yet other aspects, an assembly according to various aspects of the present disclosure may omit a suction port and/or be operated without the suction port.

Methods of Using Wound Irrigation and Debridement Assemblies

In various aspects, the present disclosure provides a method of irrigating and mechanically debriding a target body region. The method is described on the context of the assembly 110 of FIGS. 4A-4C; however, this method or a similar method may be performed using other assemblies of the present disclosure.

The method may include assembling the device 114 to the wound irrigation system 112 by placing the device 114 into the open configuration, inserting the nozzle 118 an the suction port 122 at least partially into the interior volume 130, and then placing the device 114 in the closed configuration. The method may including fastening the device 114 in the closed configuration by engaging the fastener with the body 126 of the device 114. In certain variations, the method may further include adjusting an axial position of the device 114 with respect to the nozzle 118, and/or adjusting a dimension of the device 114 using the fastener. In certain aspects, assembling the device 114 to the wound irrigation system 112 can be performed one-handed.

The method includes engaging the distal surface 132 of the device 114 with the target body region in the first configuration. The method further includes discharging the irrigation fluid from the nozzle 118 and transferring the irrigation through the interior region 130 and the first opening 134 such that the irrigation fluid contacts the target body region. In various aspects, the method may further including modifying a velocity or flow of the irrigation fluid via a suction port (not shown).

The assembly 110 may optionally be translated with respect to the target body region while the distal surface 132 maintains engagement with the target body region. In certain aspects, engagement of the compliant region 152 including the distal surface 132 with the target body region may provide a gentle mechanical debridement. The suction port 122 and tip 124 remain disengaged from the target body region to prevent sticking of the wound irrigation system 112 to the target body region.

The method further includes containing at least a portion of the irrigation fluid within the device 114. For example, the irrigation fluid and/or wound debris may be contained within the interior region 130 and/or pores of the compliant region 152. The method may further include absorbing irrigation fluid from the target body region into the pores of the compliant region 152. In certain aspects, the method may include containing substantially all of the irrigation fluid and wound debris within the device 114, such as when the device further comprises an impermeable outer layer (see, e.g., outer layer 572 of FIG. 15).

The method further includes engaging the device 114 with the target body region in the second configuration to perform mechanical debridement. The method includes compressing the compliant region 152 along the longitudinal axis 128 such that the debridement region 154 engages the target body region. The tip 124 may be translated with respect to the target body region while the compliant region 152 maintains contact with the target body region. In certain aspects, the proximal surface 136 translates together with the tip 124 while the distal surface 132 remains substantially axially fixed. A medical technician performing the method may shift the device 114 between the first and second configurations, depending on whether mechanical debridement is desired. Additionally or alternatively, the method may include rocking the device 114 side-to-side to create a scrubbing motion with the debridement region 154 while maintaining contact between the complaint region 152 and the target body region. In certain aspects, the device 114 may be shifted between configurations without changing a suction pressure. More particularly, the device 114 may be manipulated to bring the debridement region 154 into contact with the target wound region rather than applying pressure to drawn the target body region toward the debridement region 154.

The method may further include selectively engaging the device 114 with the target body region in the third configuration to increase an intensity of the mechanical debridement. The method may include compressing the compliant region 152 along the longitudinal axis 128 to engage the nozzle 118 with the debridement region 154. The method may further include applying a force to the assembly (e.g., through the wound irrigation system 112) to increase a pressure of the mechanical debridement, or removing or reducing the force to decrease the pressure. The method may include returning the device 114 to the first or second configuration, and repeating the configurations as desired.

The method may further include actuating a vacuum to remove at least a portion of the irrigation fluid and/or wound debris from the target body region. The method may include maintaining engagement between the distal surface 132 and the target body region. The method may further include axially compressing the compliant region 152 to improve a fluid seal between the device 114 and the target body region. The method may include applying negative pressure to the interior region 130 to draw the irrigation fluid and wound debris inward toward the suction port 122 and through the inlet tube 120.

The method may include disengaging the device 114 from the target body region. The method may further comprise disassembling the device 114 from the wound irrigation system 112. The method may further comprise cleaning the device 114, or optionally disposing of the device 114.

All possible combinations discussed and enumerated above and herein as optional features of the inventive devices and assemblies of the present disclosure are specifically disclosed as embodiments. In various aspects, the present disclosure contemplates a device for wound irrigation and debridement comprising a body. The body extends along a longitudinal axis. The body comprises an interior region comprising a first opening such that that the interior region and the first opening are configured to transfer an irrigation fluid. The body comprises a compliant region and a debridement region. The compliant region has a first stiffness and defines a distal surface. The compliant region includes the distal surface. The debridement region has a second stiffness different than the first stiffness. In a first configuration, the compliant region defines a first axial dimension along the longitudinal axis, the distal surface of the compliant region engages a target region, and the debridement region is axially offset from the distal surface and disengaged from the target region. In a second configuration, the compliant region is compressed along the longitudinal axis to define a second axial dimension less than the first axial dimension, thereby engaging the debridement region with the target region, and the distal surface of the compliant region engages the target region. Also specifically disclosed are combinations including this device optionally with any one or any combination of more than one of the enumerated features (1)-(12).

The device of the first embodiment optionally has any one or any combination of more than one of the following features: (1) the second stiffness is greater than the first stiffness; (2) the compliant region is porous and defines a plurality of pores, optionally the compliant region comprises an open cell foam comprising the plurality of pores, optionally the pores of the plurality of pores have an average diameter of greater than or equal to about 0.2 mm to less than or equal to about 1 mm, optionally the compliant region has a porosity of greater than or equal to about 80%; (3) the compliant region comprises a polymer selected form the group consisting of: polyurethane, polyethylene, cellulose, silicone, thermoplastic elastomer, thermoplastic polyurethane, polyvinyl chloride (PVC), and combinations thereof; (4) the compliant region comprises a first material and the debridement region comprises a second material, the first and second materials being distinct from one another; (5) the compliant region further comprises an inner surface at least partially defining the interior region, the debridement region is coupled to the inner surface and extends inward toward the longitudinal axis from the inner surface, and the debridement region defines a central opening substantially coaxial with the first opening; (6) the compliant region defines a cavity extending from the distal surface, the cavity is disposed outward of the interior region with respect to the longitudinal axis, and the debridement region is disposed within the cavity; (7) at least a portion of the body defines a substantially cylindrical shape, optionally the debridement region defines a substantially annular shape and has a second opening substantially coaxial with the first opening; (8) the debridement region comprises a plurality of discrete debridement regions distributed about the longitudinal axis; (9) the debridement region comprises at least one of: a plurality of bristles, a plurality of protrusions, a plurality of non-woven fibers, a plurality of woven fibers, a mesh, an open cell foam, a closed cell foam, a plurality of particles, or a surface coating; (10) the device further comprises a frame embedded in the compliant region, the frame is disposed outward of the interior region with respect to the longitudinal axis, the frame comprises a ductile material, and the frame is configured to be deformed to modify a shape of the compliant region; (11) the device further comprises a fastener engaging the body, optionally the fastener extends around an outer surface of the body and the fastener is configured to compress the body to reduce a dimension of the body; and/or (12) the device further comprises an impermeable layer disposed on at least a portion of an outer surface of the body.

In various aspects, the present disclosure contemplates a device for wound irrigation and debridement comprising a body. The body extends along a longitudinal axis. The body comprises an interior region and an opening such that that the interior region and the opening are configured to transfer an irrigation fluid. The body comprises a compliant region and a debridement region. The compliant region has a first density and defines a distal surface. The debridement region has a second density greater than the first density. In a first configuration, the compliant region defines a first axial dimension along the longitudinal axis, the distal surface of the compliant region engages a target region, and the debridement region is axially offset from the distal surface and disengaged from the target region. In a second configuration, the compliant region is compressed along the longitudinal axis to define a second axial dimension less than the first axial dimension, thereby engaging the debridement region with the target region, and the distal surface of the compliant region engages the target region. Also specifically disclosed are combinations including this device optionally with any one or any combination of more than one of the enumerated features (2)-(12) above.

In various aspects, the present disclosure contemplates a device for wound irrigation and debridement comprising a body. The body extends along a longitudinal axis. The body comprises an interior region and an opening such that the interior region and the opening are configured to transfer an irrigation fluid. The body comprises a compliant region and a debridement region. The compliant region comprises a first material and defines a distal surface. The debridement region is coupled to a surface of the compliant region. The debridement region comprises a second material different from the first material. In a first configuration, the compliant region defines a first axial dimension along the longitudinal axis, the distal surface of the compliant region engages a target region, and the debridement region is axially offset from the distal surface and disengaged from the target region. In a second configuration, the compliant region is compressed along the longitudinal axis to define a second axial dimension less than the first axial dimension, thereby engaging the debridement region with the target region, and the distal surface of the compliant region engages the target region. Also specifically disclosed are combinations including this device optionally with any one or any combination of more than one of the enumerated features (2)-(3) and (5)-(12) above.

In various aspects, the present disclosure contemplates in certain variations a device and nozzle assembly for wound irrigation. The assembly comprises a nozzle and a device. The nozzle is configured to receive irrigation fluid and deliver the irrigation fluid to a target region. The device is coupled to the nozzle. The device comprises a body extending along a longitudinal axis. The body includes an interior region and an opening, such that the interior region and the opening are configured to transfer the irrigation fluid. The device comprises a compliant region defining a first stiffness and defining a distal surface. At least one of the nozzle and the device comprises a debridement region defining a second stiffness different than the first stiffness. In a first configuration, the compliant region defines a first axial dimension along the longitudinal axis, the distal surface of the compliant region engages the target region, and the debridement region is axially offset from the distal surface and disengaged from the target region. In a second configuration, the compliant region is compressed along the longitudinal axis to define a second axial dimension less than the first axial dimension, thereby engaging the debridement region with the target region, and the distal surface of the compliant region engages the target region. Also specifically disclosed are combinations including this assembly optionally with any one or any combination of more than one of the enumerated features (2)-(12) as described below and (13)-(16) as described below.

The assembly optionally has any one or any combination of more than one of the following features: (13) the nozzle comprises the debridement region and the debridement region is disposed on a distal end of the nozzle; (14) the body defines the debridement region, the body is configured to engage the target region in the first configuration, the second configuration, and a third configuration, and in the third configuration, the compliant region is compressed along the longitudinal axis to define a third axial dimension less than the second axial dimension, thereby engaging the nozzle with the debridement region and the debridement region with the target region, and the distal surface of the compliant region engages the target region; (15) the interior region of the body is configured to receive a vacuum port, and the compliant region is configured to conform to the target region to create a fluid seal and pull negative pressure; and/or (16) the device further comprises a tip defining a passage, the tip is in fluid communication with the nozzle, and the tip is disposed at least partially within the interior region of the body, optionally the debridement region circumferentially surrounds at least a portion of the tip, optionally a portion of the debridement region is disposed within the passage.

In various aspects, the present disclosure provides a method of irrigating and debriding a target region. The method comprises engaging a distal surface of an assembly with the target region. The assembly includes a nozzle and a device coupled to the nozzle. The device comprises a body extending along a longitudinal axis. The body includes an interior region and an opening. The body comprises a compliant region having a first stiffness and a debridement region having a second stiffness different than the first stiffness. The compliant region defines a distal surface. The debridement region is disengaged from the target region. The method further includes discharging an irrigation fluid from the nozzle. The irrigation fluid is transferred through the interior region and the opening to contact the target region. The method further includes containing at least a portion of the irrigation fluid within one or both of the interior region and the compliant region. The method further includes compressing the device along the longitudinal axis such that the debridement region engages the target region. Optionally, the target region comprises a wound bed. Also specifically disclosed are combinations including the assembly of this method optionally with any one or any combination of more than one of the enumerated features (2)-(16).

In various aspects, the present disclosure provides an irrigation and debridement assembly comprising a nozzle, a suction port, a tip, and a device. The nozzle is configured to receive irrigation fluid and deliver the irrigation fluid to a target region. The suction port is configured to remove irrigation fluid from the target region. The tip is coupled to the suction port and the nozzle. The tip defines a passage in fluid communication with the suction port and the nozzle. The device is coupled to the tip. The device is configured to transfer irrigation fluid between the passage and the target region. The device comprises a compliant region and a debridement region. The compliant region defines a distal surface. The debridement region is coupled to the compliant region. The debridement region defines a debridement surface. In a first configuration, at least a portion of the debridement surface is offset from the distal surface by a distance. In a second configuration, the debridement surface and the distal surface cooperate to define a contact surface. The contact surface is configured to engage at least a portion of the target region. The device is movable between the first configuration and the second configuration by translating the at least a portion of the debridement surface with respect to the distal surface. Also specifically disclosed are combinations including this stretchable composite material optionally with any one or any combination of more than one of the enumerated features (2)-(16) above and (17)-(19) as described below.

The assembly optionally has any one or any combination of more than one of the following features: (17) the debridement region circumferentially surrounds at least a portion of a periphery of the tip; (18) in a wrapped position, a surface of the compliant region is substantially cylindrical and in a relaxed position, the surface is substantially planar; and/or (19) at least a portion of the debridement region is disposed in the passage of the tip.

The details, examples and preferences provided above in relation to any particular one or more of the stated aspects of the present invention, and described and exemplified below in relation to any particular one or more of the stated aspects of the present invention, apply equally to all aspects of the present invention.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A device for wound irrigation and debridement, the device comprising:
    a body extending along a longitudinal axis, the body comprising an interior region, a first opening, and a second opening such that that the interior region and the first opening are configured to transfer an irrigation fluid, the interior region extending continuously along the longitudinal axis between the first opening and the second opening, the body defining a seam parallel to the longitudinal axis, the seam configured to be opened to provide access to the interior region, wherein the seam comprises a first seam surface and a second seam surface, wherein the body has an open configuration wherein the first seam surface and the second seam surface are separated and the body extends between the first seam surface and the second seam surface; and a closed configuration in which the first and second seam surfaces are in contact with one another, the open configuration allowing removal of the body from the device, the closed configuration allowing the body to be fixed to the device, the body comprising,
        a compliant region having a first stiffness and defining a distal surface, and
        a debridement region having a second stiffness different than the first stiffness, wherein:
    in a first configuration, the compliant region defines a first axial dimension along the longitudinal axis, the distal surface of the compliant region engages a target region, and the debridement region is axially offset from the distal surface and disengaged from the target region;
    in a second configuration, the compliant region is compressed along the longitudinal axis to define a second axial dimension less than the first axial dimension, thereby engaging the debridement region with the target region, and the distal surface of the compliant region engages the target region; and
    the device is configured to be moved from the first configuration to the second configuration by compression of the compliant region from the first axial dimension to the second axial dimension.
2. The device of claim 1, wherein the second stiffness is greater than the first stiffness.
3. The device of claim 1, wherein the compliant region is porous and defines a plurality of pores.
4. The device of claim 3, wherein the compliant region comprises an open cell foam comprising the plurality of pores.
5. The device of claim 3, wherein the pores of the plurality of pores have an average diameter of greater than or equal to about 0.2 mm to less than or equal to about 1 mm.
6. The device of claim 3, wherein the compliant region has a porosity of greater than or equal to about 80%.
7. The device of claim 1, wherein the compliant region comprises a polymer selected form the group consisting of: polyurethane, polyethylene, cellulose, silicone, thermoplastic elastomer, thermoplastic polyurethane, polyvinyl chloride (PVC), and combinations thereof.
8. The device of claim 1, wherein the compliant region comprises a first material, the debridement region comprises a second material, and the first and second materials are distinct from one another.
9. The device of claim 1, wherein the compliant region further comprises an inner surface at least partially defining the interior region, and the debridement region is coupled to the inner surface and extends inward toward the longitudinal axis from the inner surface, the debridement region defining a central opening substantially coaxial with the first opening.
10. The device of claim 1, wherein compliant region defines a cavity extending from the distal surface, the cavity being disposed outward of the interior region with respect to the longitudinal axis, and the debridement region is disposed within the cavity.
11. The device of claim 1, wherein at least a portion of the body defines a substantially cylindrical shape.
12. The device of claim 11, wherein the debridement region defines a substantially annular shape.
13. The device of claim 1, wherein the debridement region comprises a plurality of discrete debridement regions distributed about the longitudinal axis.
14. The device of claim 1, wherein the debridement region comprises at least one of: a plurality of bristles, a plurality of protrusions, a plurality of non-woven fibers, a plurality of woven fibers, a mesh, an open cell foam, a closed cell foam, a plurality of particles, or a surface coating.
15. The device of claim 1, further comprising a frame embedded in the compliant region, the frame being disposed outward of the interior region with respect to the longitudinal axis, the frame comprising a ductile material and being configured to be deformed to modify a shape of the compliant region.
16. The device of claim 1, further comprising a fastener engaging the body.
17. The device of claim 16, wherein the fastener extends around an outer surface of the body, the fastener being configured to compress the body to reduce a dimension of the body.
18. The device of claim 1, further comprising an impermeable layer disposed on at least a portion of an outer surface of the body.
19. The device of claim 1, wherein the compliant region is configured to conform to the target region.
20. The device of claim 1, wherein the distal surface of the compliant region is configured to form a seal with the target region.
21. A device for wound irrigation and debridement, the device comprising:
    a body extending along a longitudinal axis, the body comprising an interior region, a first opening, and a second opening such that that the interior region and the first opening are configured to transfer an irrigation fluid, the interior region extending continuously along the longitudinal axis between the first opening and the second opening, the body defining a seam parallel to the longitudinal axis, the seam configured to be opened to provide access to the interior region, wherein the seam comprises a first seam surface and a second seam surface, wherein the body has an open configuration wherein the first seam surface and the second seam surface are separated and the body extends between the first seam surface and the second seam surface; and a closed configuration in which the first and second seam surfaces are in contact with one another, the open configuration allowing removal of the body from the device, the closed configuration allowing the body to be fixed to the device, the body comprising, a compliant region having a first density and defining a distal surface, and a debridement region having a second density greater than the first density, wherein:

in a first configuration, the compliant region defines a first axial dimension along the longitudinal axis, the distal surface of the compliant region engages a target region, and the debridement region is axially offset from the distal surface and disengaged from the target region;

in a second configuration, the compliant region is compressed along the longitudinal axis to define a second axial dimension less than the first axial dimension, thereby engaging the debridement region with the target region, and the distal surface of the compliant region engages the target region; and the device is configured to be moved from the first configuration to the second configuration by compression of the compliant region from the first axial dimension to the second axial dimension.

22. A device for wound irrigation and debridement, the device comprising:

a body extending along a longitudinal axis, the body comprising an interior region, a first opening, and a second opening such that that the interior region and the first opening are configured to transfer an irrigation fluid, the interior region extending continuously along the longitudinal axis between the first opening and the second opening, the body defining a seam parallel to the longitudinal axis, the seam configured to be opened to provide access to the interior region, wherein the seam comprises a first seam surface and a second seam surface, wherein the body has an open configuration wherein the first seam surface and the second seam surface are separated and the body extends between the first seam surface and the second seam surface; and a closed configuration in which the first and second seam surfaces are in contact with one another, the open configuration allowing removal of the body from the device, the closed configuration allowing the body to be fixed to the device, the body comprising, a compliant region comprising a first material and defining a distal surface, and a debridement region coupled to a surface of the compliant region, the debridement region comprising a second material different from the first material, wherein:

in a first configuration, the compliant region defines a first axial dimension along the longitudinal axis, the distal surface of the compliant region engages a target region, and the debridement region is axially offset from the distal surface and disengaged from the target region;

in a second configuration, the compliant region is compressed along the longitudinal axis to define a second axial dimension less than the first axial dimension, thereby engaging the debridement region with the target region, and the distal surface of the compliant region engages the target region; and the device is configured to be moved from the first configuration to the second configuration by compression of the compliant region from the first axial dimension to the second axial dimension.

* * * * *